(12) United States Patent
Kuehn et al.

(10) Patent No.: US 10,800,656 B2
(45) Date of Patent: *Oct. 13, 2020

(54) COMPOSITIONS COMPRISING IONIC LIQUIDS FOR DECOMPOSING PEROXIDES

(71) Applicant: DIEHL AVIATION GILCHING GMBH, Gilching (DE)

(72) Inventors: Fritz Kuehn, Garching (DE); Florian J. Groche, Munich (DE); Christoph Kallfass, Schwaebisch Hall (DE)

(73) Assignee: Diehl Aviation Gilching GmbH, Gilching (DE)

( * ) Notice: Subject to any disclaimer, the term of this patent is extended or adjusted under 35 U.S.C. 154(b) by 259 days.

This patent is subject to a terminal disclaimer.

(21) Appl. No.: 15/815,740

(22) Filed: Nov. 17, 2017

(65) Prior Publication Data
US 2018/0141811 A1 May 24, 2018

(30) Foreign Application Priority Data
Nov. 18, 2016 (EP) .................................... 16199630

(51) Int. Cl.
| | | |
|---|---|---|
| C01B 13/02 | (2006.01) | |
| C01B 15/01 | (2006.01) | |
| C01B 15/10 | (2006.01) | |
| C01B 15/12 | (2006.01) | |
| B01J 31/02 | (2006.01) | |

(Continued)

(52) U.S. Cl.
CPC ............ *C01B 13/0225* (2013.01); *A62B 7/08* (2013.01); *A62B 21/00* (2013.01); *B01J 31/0281* (2013.01); *B01J 31/0298* (2013.01); *C01B 13/0211* (2013.01); *C01B 15/01* (2013.01); *C01B 15/103* (2013.01); *C01B 15/12* (2013.01); *C07D 233/58* (2013.01); *B01J 2531/16* (2013.01); *B01J 2531/842* (2013.01)

(58) Field of Classification Search
None
See application file for complete search history.

(56) References Cited

U.S. PATENT DOCUMENTS 2,035,896 A   3/1936   Kerwin
4,548,730 A   10/1985  Koslow
(Continued)

FOREIGN PATENT DOCUMENTS

CN   105776144 a   7/2016
DE   3837432 A1    5/1990
(Continued)

OTHER PUBLICATIONS

European Search Report for Applicaiton No. 16199633.5-1354 dated Feb. 17, 2017, 18 pages.
(Continued)

*Primary Examiner* — Joseph D Anthony
(74) *Attorney, Agent, or Firm* — Laurence A. Greenberg; Werner H. Stemer; Ralph E. Locher

(57) ABSTRACT

The invention relates to a composition for generating oxygen, comprising at least one oxygen source, and at least one ionic liquid comprising a cation and an anion, wherein the oxygen source is a peroxide compound, the ionic liquid is in the liquid state at least in a temperature range from −10° C. to +50° C., and the anion is selected from metallate anions.

15 Claims, 19 Drawing Sheets

(51) Int. Cl.
*A62B 7/08* (2006.01)
*A62B 21/00* (2006.01)
*C07D 233/58* (2006.01)

(56) References Cited

U.S. PATENT DOCUMENTS

| | | | |
|---|---|---|---|
| 4,963,327 A | 10/1990 | Russell | |
| 8,147,760 B1 | 4/2012 | Huvard et al. | |
| 10,479,682 B2 * | 11/2019 | Kallfass | C01B 13/0203 |
| 10,544,044 B2 * | 1/2020 | Kuehn | C25B 1/02 |
| 10,544,511 B2 * | 1/2020 | Kuehn | C01B 13/0214 |
| 2007/0007135 A1 | 1/2007 | Gheczy et al. | |
| 2010/0283003 A1 * | 11/2010 | Siemer | C07D 233/58 |
| | | | 252/186.1 |
| 2011/0017209 A1 | 1/2011 | Monzyk | |
| 2011/0073331 A1 | 3/2011 | Xu | |
| 2018/0141810 A1 * | 5/2018 | Kuehn | B01J 23/002 |
| 2019/0016596 A1 * | 1/2019 | Kallfass | B01J 23/007 |
| 2020/0031665 A1 * | 1/2020 | Kallfass | B01J 23/75 |
| 2020/0031667 A1 * | 1/2020 | Kallfass | C01B 13/0225 |

FOREIGN PATENT DOCUMENTS

| | | | |
|---|---|---|---|
| DE | 19602149 A1 | 7/1997 | |
| DE | 102006042320 A1 | 3/2008 | |
| DE | 102009041065 A1 | 3/2011 | |
| EP | 0306840 A2 | 3/1989 | |
| EP | 2856867 A1 | 4/2015 | |
| JP | S6177604 A | 4/1986 | |
| JP | 61236602 A | 10/1986 | |
| JP | S61227903 A | 10/1986 | |
| JP | 2009138254 A | 6/2009 | |
| WO | 8602063 A1 | 4/1986 | |
| WO | 9743210 A1 | 11/1997 | |
| WO | 0240397 A1 | 5/2002 | |
| WO | 2006083663 A2 | 8/2006 | |
| WO | 2013153178 A1 | 10/2013 | |

OTHER PUBLICATIONS

European Search Report for Application No. 16199622.8-1354 dated Jan. 30, 2017, 7 pages.
European Search Report for Application No. 16199625.1-1754 dated May 22, 2017, 12 pages.
European Search Report for Application No. 16199630.1-1354, dated Jan. 30, 2017, 7 pages.
European Search Report for Application No. 16199636.8-1354, dated Feb. 17, 2017, 18 Pages.
European Search Report for Application No. 16199637.6-1754 dated May 22, 2017, 12 pages.
European Search Report for Application No. 16199641.8-1754, dated Jun. 8, 2017, 8 pages.
Fluck, et al."New Notations in the Periodic Table" International Union of Pure and Applied Chemistry Inorganic Chemistry Division, Pure&Appl. Chem., vol. 60, No. 3, pp. 431-436, 1988.
Gaston P. Barreto et al. "Effect of ionic liquid on the termal decomposition of cyclic organic peroxides", Arabian Journal of chemistry, Jun. 1, 2016, 10 pages.
Rakhmanov, et al. "Oxidation of Dibenzothiphene with Hydrogen Peroxide in Ionic Liquids" ISSN 0965-5441, Petroleum Chemistry, 2012, vol. 52, No. 3, pp. 213-214.
Sitze, et al. "Ionic Liquids Based on FeCl3 and FeCl2. Raman Scattering and ab Initio Calculations" Inorg. Chem. 2001, 40, 2298-2304 (ReceiVed Sep. 14, 2000).

* cited by examiner

COMPOSITIONS COMPRISING IONIC LIQUIDS FOR DECOMPOSING PEROXIDES

FOREIGN PRIORITY

This application claims priority to European Patent Application No. 16199630.1 filed Nov. 18, 2016, the entire contents of which is incorporated herein by reference.

TECHNICAL FIELD

The present invention relates to compositions for generating oxygen.

BACKGROUND

Humans cannot exist without oxygen. In many environments, however, oxygen supply is insufficient or there is a risk of emergency situations involving a shortage of oxygen, for example in submarines, in mines, in space capsules, and also in air planes. Air pressure decreases with increasing flight altitude, and at cruising altitudes of many aircrafts, in particular long-range aircrafts, sufficient oxygen for human beings is no longer available. Therefore, the aircraft cabins are pressurized in order to ensure sufficient oxygen supply. In case of a sudden de-pressurization of an aircraft cabin, oxygen masks must be available, which supply oxygen to crew and passengers until the aircraft reaches a flight level where sufficient oxygen is available.

The oxygen which is provided by these emergency systems is typically produced by so-called "chlorate candles" or "oxygen candles". These chemical oxygen generators contain chlorates or perchlorates as an oxygen source, as well as various additives such as fuels, catalysts, binders and moderators. Chlorate candles are often in the form of cylindrical rods, i.e. they have a shape similar to candles. Chlorate candles are disclosed, for example, in WO 97/43210.

While chlorate candles are widely used, they require the high temperatures at which the oxygen production takes place. Namely, in chlorate candles oxygen is released at temperatures between 450° C. and 700° C. Therefore, effective heat insulation of chlorate candles is required, resulting in a weight and size penalty. Furthermore, decomposition of chlorates and perchlorates tends to produce toxic side products, in particular chlorine, which must be removed from the oxygen stream, thus additionally adding size and weight. Furthermore, there is a risk of system failure. In chlorate candles the reaction zone is normally liquid, i.e. there is a liquid zone travelling through the candle, starting at the point of ignition. The liquid zone within the otherwise solid candle considerably destabilizes the candle such that mechanical shocks or even slight vibrations may result in separation of the candle portions, thus interrupting the heat transfer and discontinuing the chlorate or perchlorate decomposition. In such a case, oxygen production may be interrupted, although oxygen is still vitally needed.

A different type of chemical oxygen generators uses peroxides as oxygen sources, for example sodium percarbonate, sodium perborate, or an urea adduct of hydrogen peroxide. Decomposition of the peroxides yields oxygen, and the decomposition reaction can be started by contacting the peroxide compounds with an appropriate enzyme or transition metal catalyst. Chemical oxygen generators of this type are disclosed in U.S. Pat. No. 2,035,896, WO 86/02063, JPS 61227903, and DE 196 02 149.

All these known peroxide-based oxygen generators have in common that they use water for providing contact between the peroxides and the catalysts. Unfortunately, water freezes at 0° C. and, therefore, no oxygen can be produced below 0° C. This is unacceptable for many emergency systems. An additional disadvantage of the aqueous systems is that the decomposition of peroxides in aqueous solutions results in vehement effervescing of the reaction mixture. As a consequence, an oxygen generating device containing a peroxide-based oxygen generating composition must have a complicated structure.

It would be beneficial to provide a solution to at least some of the problems of the prior art outlined above, and to provide a composition for generating oxygen which produces breathable oxygen reliably and continuously in a wide temperature range, and preferably including subfreezing temperatures. The oxygen produced should be at a low temperature, preferably below 150° C., and further preferably free from toxic or otherwise noxious components such as chlorine or carbon monoxide. It would be also beneficial to provide a composition capable to produce oxygen over an extended period of time and with a significant flow rate.

SUMMARY

Exemplary embodiments of the invention include a composition for generating oxygen, comprising at least one oxygen source, and at least one ionic liquid comprising a cation and an anion, wherein the oxygen source is a peroxide compound, the ionic liquid is in the liquid state at least in a temperature range from −10° C. to +50° C., and the anion is selected from metallate anions.

Exemplary embodiments of the invention are based on an entirely new concept, the use of ionic liquids for decomposing solid peroxide compounds.

Technical implementations of this inventive concept include a composition for generating oxygen, a method for generating oxygen from this composition, a device for generating oxygen containing the composition, and the use of an ionic liquid as a dispersant or solvent and/or as a heat sink in the composition and/or for releasing oxygen from the composition over an extended period of time.

Implementations of this inventive concept also include the composition being in the form of a kit, i.e. in a form preventing that all constituents of the composition, which are required for initiating and supporting oxygen generation, can come into physical contact with each other.

Implementations of this invention further include that the kit is specifically adapted for filling or refilling a device for generating oxygen according to this invention.

As can be easily understood, the constituents of the composition are the same, irrespective of which technical implementation of the invention is contemplated. Therefore, any disclosure provided for a particular implementation (such as composition, device, method or use) is analogously applicable to the other implementations of this invention.

Embodiments 1 to 65 below constitute exemplary implementations of this invention.

1. A composition for generating oxygen, comprising
   at least one oxygen source, and
   at least one ionic liquid comprising a cation and an anion,
      wherein
      the oxygen source is a peroxide compound,
      the ionic liquid is in the liquid state at least in a temperature range from −10° C. to +50° C., and
      the anion is selected from metallate anions.
2. The composition according to embodiment 1, wherein the oxygen source and the ionic liquid are not in physical contact with each other.

3. The composition according to embodiment 1 or 2, wherein the oxygen source is selected from alkali metal percarbonates, alkali metal perborates, urea hydrogen peroxide, and mixtures thereof.

4. The composition according to any one of embodiments 1 to 3, wherein the oxygen source is one or more of Na2CO3×1.5H2O2, NaBO3×4 H2O, NaBO3×H2O, and urea hydrogen peroxide.

5. The composition according to any one of embodiments 1 to 4, wherein the cation is selected from the group consisting of heterocyclic hydrocarbon cations, ammonium, and phosphonium cations.

6. The composition according to any one of embodiments 1 to 5, wherein the cation has at least one substituent.

7. The composition according to any one of embodiments 1 to 6, wherein the cation is symmetrically or asymmetrically disubstituted.

8. The composition according to embodiment 6 or 7, wherein the substituents are independently selected from optionally substituted alkyl groups having 1 to 18 carbon atoms.

9. The composition according to any one of embodiments 1 to 8, wherein the cation is selected from the group consisting of imidazolium, pyrrolidinium, ammonium, choline, pyridinium, pyrazolium, piperidinium, phosphonium, sulfonium cations.

10. The composition according to any one of embodiments 1 to 9, wherein the metallate anion comprises at least one transition metal and at least one halide ion and/or pseudohalide ion.

11. The composition according to embodiment 10, wherein the transition metal is selected from iron and copper.

12. The composition according to embodiment 10 or 11, wherein the halide is selected from the group consisting of chloride, bromide and iodide and/or the pseudohalide is selected from the group consisting of cyanide, isocyanide, thiocyanate, and isothiocyanate.

13. The composition according to any one of embodiments 1 to 12, wherein the ionic liquid has the general formula $zC^+ MX_y^{z-}$, wherein C represents a monovalent cation, M is selected from the group consisting of $Fe^{3+}$, $Fe^{2+}$ and $Cu^+$, and
when M is $Fe^{3+}$, y=4 and z=1,
when M is $Fe^{2+}$, y=4 and z=2, and
when M=$Cu^+$, y=2 and z=1.

14. The composition according to embodiment 13, wherein C represents a N,N'-disubstituted imidazolium cation.

15. The composition according to embodiments 14, wherein the substituents are independently selected from the group consisting of methyl, hydroxy ethyl, butyl, hexyl, and octyl groups.

16. The composition according to any one of embodiments 1 to 15 wherein the composition comprises at least one ionic liquid not having a metallate anion.

17. The composition according to any one of embodiments 1 to 16, wherein the oxygen source is present in an amount ranging from 1 to 99 weight % of the composition and the ionic liquid is present in an amount ranging from 99 to 1 weight % of the composition.

18. The composition according to any one of embodiments 1 to 17, wherein the oxygen source is in the form of a powder or in the form at least one powder compact.

19. The composition according to embodiment 18, wherein the at least one powder compact has been compacted with a pressure in the range from 1 to 220 MPa.

20. The composition according to any one of embodiments 1 to 19, wherein the oxygen source is a hydrogen peroxide adduct compound.

21. The composition according to any one of embodiments 1 to 20, wherein the composition is provided as a kit of at least two physically separated formulations, one of the formulations comprising the ionic liquid having a metallate anion, and the other formulation comprising the oxygen source.

22. The composition according to any one of embodiments 1 to 21, wherein the oxygen source is an oxygen source formulation comprising two or more peroxide compounds and, optionally, at least one additive.

23. The composition according to any one of embodiments 1 to 22, wherein the ionic liquid is an ionic liquid formulation comprising at least one active ionic liquid and, optionally, at least one non-active ionic liquid and, further optionally, at least one additive.

24. A method for generating oxygen, comprising
providing at least one oxygen source,
providing at least one ionic liquid, the ionic liquid comprising a cation and an anion,
wherein the oxygen source is a peroxide compound, the ionic liquid is in the liquid state at least in a temperature range from −10° C. to +50° C., and the anion is selected from metallate anions, and
contacting the oxygen source and the ionic liquid.

25. The method according to embodiment 24, wherein the oxygen source is selected from alkali metal percarbonates, alkali metal perborates, urea hydrogen peroxide, and mixtures thereof.

26. The method according to embodiments 24 or 25, wherein the oxygen source is one or more of Na2CO3× 1.5H2O2, NaBO3×4 H2O, NaBO3×H2O, and urea hydrogen peroxide.

27. The method according to any one of embodiments 24 to 26, wherein the cation is selected from the group consisting of heterocyclic hydrocarbon cations, ammonium and phosphonium cations.

28. The method according to any one of embodiments 24 to 27, wherein the cation has at least one substituent.

29. The method according to any one of embodiments 24 to 28, wherein the cation is symmetrically or asymmetrically disubstituted.

30. The method according to embodiments 28 or 29, wherein the substituents are independently selected from optionally substituted alkyl groups having 1 to 18 carbon atoms.

31. The method according to any one of embodiments 24 to 30, wherein the cation is selected from the group consisting of imidazolium, pyrrolidinium, ammonium, choline, pyridinium, pyrazolium, piperidinium, phosphonium, sulfonium cations.

32. The method according to any one of embodiments 24 to 31, wherein the metallate anion comprises at least one transition metal and at least one halide ion and/or pseudohalide ion.

33. The method according to embodiment 32, wherein the transition metal is selected from iron and copper.

34. The method according to embodiment 32 or 33, wherein the halide is selected from the group consisting of chloride, bromide, and iodide, and/or the pseudohalide is selected from the group consisting of cyanide, isocyanide, thiocyanate and isothiocyanate.

35. The method according to any one of embodiments 24 to 34, wherein the ionic liquid has the general formula $zC^+$ $MX_y^{z-}$, wherein C represents a monovalent cation, M is selected from the group consisting of $Fe^{2+}$, $Fe^{3+}$ and $Cu^+$, and when M is $Fe^{3+}$, y=4 and z=1,
when M is $Fe^{2+}$, y=4 and z=2, and
when $M=Cu^+$, y=2 and z=1.

36. The method according to embodiment 35, wherein C represents a N,N'-disubstituted imidazolium cation.

37. The method according to embodiment 36, wherein the substituents are independently selected from the group consisting of methyl, hydroxyalkyl, hydroxy ethyl, butyl, hexyl, and octyl groups.

38. The method according to any one of embodiments 24 to 37 wherein the composition comprises at least one ionic liquid not having a metallate anion.

39. The method according to any one of embodiments 24 to 38, wherein the oxygen source is present in an amount ranging from 1 to 99 weight % of the composition and the ionic liquid is present in an amount ranging from 99 to 1 weight % of the composition.

40. The method according to any one of embodiments 24 to 39, wherein the oxygen source is in the form of a powder or in the form at least one powder compact.

41. The method according to embodiment 40, wherein the at least one powder compact has been compacted with a pressure in the range of 1 to 220 MPa.

42. Use of a ionic liquid comprising a cation and an anion, wherein the anion is selected from metallate anions, as an initiator of a decomposition reaction of a peroxide compound, and as a heat sink for dissipating the reaction heat.

43. The use of embodiment 42, wherein the ionic liquid is an ionic liquid as defined in any one of embodiments 27 to 38, and the oxygen source is a hydrogen peroxide adduct compound as defined in embodiment 25 or 26.

44. A device for generating oxygen, comprising
at least one reaction chamber for housing a composition for generating oxygen, the composition an oxygen source formulation and an ionic liquid formulation, the oxygen source formulation comprising a peroxide compound, and the ionic liquid formulation comprising an ionic liquid having a cation and a metallate anion,
means for maintaining the oxygen source formulation and the ionic liquid formulation physically separated from each other,
means for establishing physical contact of the oxygen source formulation and the ionic liquid formulation, and
means for allowing oxygen to exit the reaction chamber.

45. The device according to embodiment 44, wherein the means for allowing oxygen to exit the reaction chamber is a gas permeable membrane or a frit, which is gas permeable and liquid tight.

46. The device according to embodiment 44 or 45, wherein the reaction chamber comprises a first compartment for receiving one of the oxygen source formulation and the ionic liquid formulation and a second compartment for receiving the other one of the oxygen source formulation and the ionic liquid formulation.

47. The device according to any one of embodiments 44 to 46, wherein the means for maintaining the oxygen source formulation and the ionic liquid formulation physically separated comprise at least one receptacle within the chamber for receiving one of the oxygen source formulation and the ionic liquid formulation.

48. The device according to any one of embodiments 44 to 47 wherein the means for maintaining one of the oxygen source formulation and the ionic liquid formulation physically separated comprise a membrane, a metal or plastic foil, or a glass sheet between the first compartment and the second compartment.

49. The device according to any one of embodiments 44 to 48, wherein the means for establishing physical contact comprise a device for destroying the means for maintaining the oxygen source formulation and the ionic liquid formulation physically separated, and an activation mechanism for activating the device.

50. The device according to any one of embodiments 44 to 49 wherein the device for destroying is a solid plate, a grid, a cutting edge, or a firing pin.

51. The device according to any one of embodiments 44 to 50 wherein, the means for establishing physical contact is a syringe or a dosing mechanism.

52. The device according to any one of embodiments 44 to 51, wherein the at least one reaction chamber is placed within a container having an oxygen outlet.

53. The device according to any one of embodiments 44 to 52, wherein at least two reaction chambers are placed within in a container having an oxygen outlet, the container providing a common gas space for receiving oxygen exiting the at least two reaction chambers.

54. The device according to embodiment 53, comprising from 3 to 20 reaction chambers.

55. The device according to embodiment 53 or 54, wherein the at least two reaction chambers comprise two different compositions for generating oxygen.

56. The device according to embodiment 55, wherein the different compositions for generating oxygen differ either in the type of ionic liquid having a metallate anion or in type of peroxide compound, or in degree of compaction of the oxygen source.

57. The device according to any one of embodiments 44 to 56 wherein the peroxide compound is selected from alkali metal percarbonates, alkali metal perborates, urea hydrogen peroxide, and mixtures thereof.

58. The device according to embodiment 57, wherein the peroxide compound is one or more of $Na_2CO_3 \times 1.5H_2O_2$, $Na BO_3 \times 4 H_2O$, $Na BO_3 \times H_2O$, and urea hydrogen peroxide.

59. The device according to any one of embodiments 44 to 58, wherein the cation is selected from the group consisting of heterocyclic hydrocarbon cations, ammonium and phosphonium cations.

60. The device according to any one of embodiments 44 to 59, wherein the cation represents a N, N'-disubstituted imidazolium cation.

61. The device according to any one of embodiments 44 to 60, wherein the ionic liquid formulation also comprises an ionic liquid not having a metallate anion.

62. The device according to any one of embodiments 44 to 61, wherein the metallate anion comprises at least one transition metal and at least one halide ion and/or pseudo-halide ion.

63. The device according to embodiment 62, wherein the anion comprises iron or copper.

64. The device according to any one of embodiments 52 to 63 wherein the oxygen outlet comprises means for restricting gas flow.

65. Charge component for a device for generating oxygen, the charge component comprising an oxygen formulation comprising a peroxide compound and/or an ionic liquid formulation comprising an ionic liquid having a cation and a metallate anion.

A composition, method, device or use for generating oxygen in the sense of this invention is a composition, method, device or use intended for generating oxygen, while any compositions, methods, devices or uses which may generate oxygen as a side reaction do not constitute compositions, methods, devices or uses in the sense of this invention.

The oxygen generating compositions according to exemplary embodiments of the invention comprise, as the essential constituents, at least one peroxide compound as an oxygen source, and at least one ionic liquid as an initiator for a decomposition reaction of the oxygen source and for dissipating the heat generated during the peroxide decomposition reaction. The compositions are 2-component systems.

The present inventors found that peroxide compounds such as hydrogen peroxide adduct compounds can be decomposed by particular ionic liquids in a similar manner as in aqueous solution, but without the disadvantages of aqueous solutions. In particular, decomposition of peroxide compounds such as hydrogen peroxide adducts by those ionic liquids yields breathable oxygen at low temperatures, and without requiring bulky thermal insulations for the oxygen generating device. Exemplary oxygen generating compositions of this invention do not contain any water.

Ionic liquids are salts in the liquid state. Therefore, any salt that melts without decomposing or vaporizing yields an ionic liquid Sometimes, salts which are liquid below the boiling point of water are considered as ionic liquids. Technical interesting are in particular those ionic liquids which are in the liquid state at relatively low temperatures such as at room temperature or even below room temperature.

An ionic compound is considered as an ionic liquid herein when it is in the liquid state at least in a temperature range from −10° C. to +50° C. Preferred ionic liquids are in the liquid state at least from −30° C. to +70° C., and the most preferred ionic liquids are in the liquid state in an even broader temperature range such as from −70° C. to +150° C.

The properties of ionic liquids can be modified and adapted to the particular needs by varying the chemical structure. Typically, ionic liquids are thermally stable, have wide liquid regions, a high heat capacity and nearly no vapour pressure. Most of them are incombustible. They can be even used as flame retardants. Reference is made to US 2011/0073331 A1 disclosing ionic liquid flame retardants and quoting literature disclosing preparation methods (paragraph 0127).

As indicated above, the ionic liquids used in the present invention should be in the liquid state at a low temperature, preferably down to −30° C. or even below. Such ionic liquids are salts consisting of organic cations and organic anions, and both cations and anions are bulky and preferably asymmetric. As a general rule, the melting temperature decreases with increasing bulkiness and decreasing symmetry of cations and anions. Combinations of highly bulky and asymmetric cations and anions may not freeze down to temperatures as low as −120° C. Many ionic liquids are available which are liquid at −70° C. and above.

The particular ionic liquids which are able to decompose hydrogen peroxide adduct compounds and other peroxide compounds in non-aqueous systems are metallate-based ionic liquids, i.e. the anions are metallates. Metallate anions are complex anions wherein the metal is ligated to a plurality of atoms or small groups. These active ionic liquids have the general formula $$zC^+MX_y^{z-} \quad (1),$$

wherein C represents a cation, M represents a metal, and X represents a halide or a pseudohalide. The values for y, z depend on the valency of the particular metal. Typically, y and z are in a range from one to six.

Suitable cations are, for example, imidazolium, pyrrolidinium, ammonium, choline, pyridinium, pyrazolium, piperidinium, phosphonium, and sulfonium cations. The cations may or may not have substituents. Particularly, the cations may have one or more substituents. In exemplary embodiments, the cations are disubstituted. The substitution may be symmetric or asymmetric.

Exemplary substituents (side chains) are alkyl groups having from 1 to 18 carbon atoms, which may be further substituted. Such substituents are methyl, hydroxyalkyl such as hydroxyethyl, butyl, hexyl and octyl groups. Exemplary active ionic liquids have symmetrical or asymmetrical N,N'-disubstituted imidazolium cations.

The anions of the active ionic liquids comprise a transition metal. Transition metals as understood herein are those elements which have an incomplete d-shell, or which may form ions having an incomplete d-shell, including lanthanides and actinides. Exemplary transition metals are iron and copper, due to their particularly high activity. Iron may be present in the ionic liquids in the oxidation states plus 2 and plus 3, for example, and copper may be present in the oxidation state plus 1, for example. Another exemplary transition metal is titanium, for example in the oxidation state plus 1.

The anions further comprise at least two ions X, wherein X has a charge of minus 1. Exemplary ions are halides and pseudohalides. Exemplary halides are fluoride, chloride, bromide and iodide, and exemplary pseudohalides are cyanide, isocyanide, hydroxide, hydro sulfide, cyanate, isocyanate, thiocyanate, isothiocyanate, azide. The ions X in the above formula (1) may be the same or different. For example, the metallate anion may contain one halide ion and one pseudohalide ion.

Ionic liquids having a particularly high peroxide decomposition activity are N,N'-disubstituted imidazolium metallate compounds comprising iron in the oxidation state plus 2 or plus 3, or copper in the oxidation state plus 1, having formula (2) below

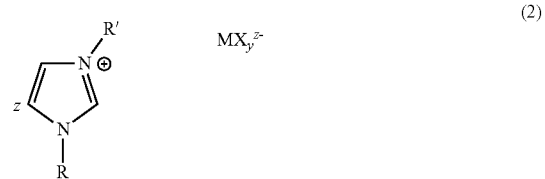

when M represents $Fe^{3+}$, y=4 and z=1,
when M represents $Fe^{2+}$, y=4 and z=2, and
when M represents $Cu^{1+}$ y=2 and z=1.

R and R' represent, independently from another, an optionally substituted alkyl group having from 1 to 18 carbon atoms, for example a methyl, hydroxyalkyl such as hydroxyethyl, butyl, hexyl, or octyl group.

Active ionic liquids having formula (1) can be prepared, for example, by reacting precursor compounds CX and MX y-z as described in Inorg. Chem., 2001, 40(10), pp 2298-2304.

One single active ionic liquid may be used to generate oxygen by decomposition of peroxides. Alternatively, different active ionic liquids may be used in combination or, further alternatively, one or more active ionic liquids may be used in combination with one or more non active ionic liquids. Non active ionic liquids are liquid salts which do not have an active metallate anion and, therefore, are not able to decompose peroxides to yield breathable oxygen. Thus, in exemplary embodiments this invention uses ionic liquid formulations comprising one or more active ionic liquids, i.e. ionic liquids having metallate anions, and optionally one or more non active ionic liquids, i.e. ionic liquids not having metallate anions.

Non active ionic liquids which may be used in combination with the active ionic liquids are not particularly limited. It is only required that they are liquid in the desired temperature range, and they do not react with any constituents of the oxygen generating composition, or with a reaction product or intermediate product of the peroxide decomposition reaction.

Suitable cations for the non active ionic liquids are, for example, the same cations indicated above for the active ionic liquids. Suitable anions include dimethylphosphate, methylsulfate, trifluoromethylsulfonate, bis(trisfluoromethylsulfonyl)imide, chloride, bromide, iodide, tetrafluoroborate, and hexafluorophosphate. In the case of "small" anions such as chloride, bromide, and iodide, particularly bulky cations can be selected, in order to provide for the desired low temperature liquidity.

Some exemplary non active ionic liquids are
butyltrimethylammoniumbis(trifluoromethylsulfonyl)imide
1-butyl-3-methylimidazoliumtrifluoromethanesulfonate,
1-butyl-3-methylimidazoliumdimethylphosphate,
1-butyl-3-methylimidazoliummethylsulfate,
1,1-butylmethylpyrrolidiniumbis(trifluoromethylsulfonyl) imide,
1,3-dimethylimidazoliumdimethylphosphate,
1,3-dimethylimidazoliummethylsulfate.

In exemplary embodiments, at least one solid hydrogen peroxide adduct compound is used as an oxygen source. Solid hydrogen peroxide adduct compounds constitute suitable and stable substituents for liquid hydrogen peroxide, are easily storable, long term stable and safe to work with. Exemplary oxygen sources are alkali metal percarbonates, e.g. sodium percarbonate ($Na_2CO_3 \times 1.5H_2O_2$), alkali metal perborates, e.g. sodium perborate ($NaBO_3 \times 4H_2O$, $NaBO_3 \times H_2O$), and urea hydrogen peroxide (UHP). In UHP urea and hydrogen peroxide are present in a molar ratio of about 1:1.

The peroxide compounds are not particularly limited, as long as they are stable under usual storage conditions, preferably also at elevated temperatures for example in the vicinity of a fire. The peroxide compounds can be used singly or in combinations of two or more, i.e. as oxygen source formulations. Such formulations may contain further additives which do not detrimentally interfere with the peroxide decomposition reaction. The peroxide compounds can be soluble or partially soluble or insoluble in the active and non active ionic liquids.

In exemplary embodiments, the compositions for generating oxygen may comprise from about 1 to 99 weight % of one or more oxygen sources, from about 99 to 1 weight % of one or more active ionic liquids, and optionally from about 1 to 98 weight % of one or more non active ionic liquids. In further exemplary embodiments, the oxygen source or mixture of oxygen sources constitutes from 15 to 45 weight %, the active ionic liquids or mixture of active ionic liquids constitutes from 55 to 85 weight %, and the non active ionic liquid constitutes from 0 to 84 weight % of the composition. Optionally, further constituents may be present, for example silicone dioxide. In exemplary embodiments the amounts of such additional constituents do not exceed about 20 weight % of the composition.

In the context herein, the term "composition" includes conditions wherein the oxygen source and the active ionic liquid are in contact with each other, as well as conditions wherein the oxygen source and the active ionic liquid are not in contact with each other, i.e. the oxygen source and the active ionic liquid constitute a kit of parts.

When a peroxide compound such as solid hydrogen peroxide adduct compound comes in contact with an active ionic liquid having a metallate anion, decomposition of the peroxide compound proceeds. Therefore, the constituents of the composition for generating oxygen shall be stored in a condition wherein the active ionic liquid can not trigger the release of oxygen from the peroxide compound. In exemplary embodiments, this is achieved by providing the composition for generating oxygen in the form of a "kit of parts" i.e. as a combination of two components, with one component comprising the at least one oxygen source, and the other component comprising the at least one active ionic liquid. The kit may optionally comprise one or more further constituents, for example a non active ionic liquid. In exemplary embodiments any further constituents of the composition for generating oxygen are admixed to either the oxygen source or the active ionic liquid, or both.

As exemplary further constituents may be mentioned silicon dioxide (as a heat sink), resorcinol (as a radical scavenger), 2-methyl-hydrochinone, eugenol, phenol and 4-propylphenol, all of them reducing the reaction rate.

Accordingly, an exemplary method for generating oxygen according to the present invention comprises providing at least one oxygen source, providing at least one active ionic liquid comprising a metallate anion, wherein the oxygen source is a peroxide compound, and the active ionic liquid is in the liquid state at least in the temperature range from −10° C. to +50° C., and contacting the oxygen source and the ionic liquid.

An exemplary device for generating oxygen according to the present invention is specifically adapted for housing the essential constituents of the composition for generating oxygen, i.e. the at least one oxygen source and the at least one active ionic liquid, in a physically separated state, and bringing them into physical contact once generation of oxygen is desired.

An exemplary device comprises at least one reaction chamber. The reaction chamber may have one single compartment or two compartments separated from one another by a membrane or another liquid tight means which can be easily destroyed, for example a thin metal or plastic foil or a thin glass plate. Alternatively, the reaction chamber may contain at least one receptacle for receiving one of the essential constituents of the composition for generating oxygen, i.e. the at least one oxygen source or the at least one active ionic liquid, and optionally any additives. By placing one of the oxygen source and the active ionic liquid in a sealable receptacle, while the other essential constituent is outside the receptacle, or alternatively, by placing one of the constituents of the composition for generating oxygen in a first compartment of the reaction chamber, while the other essential constituent is placed in a second compartment of the reaction chamber, the essential constituents are maintained physically separated, and a decomposition reaction of the peroxide compound is prevented.

In order to allow the generation of oxygen, physical contact of the essential constituents of the composition for generating oxygen, i.e. of the peroxide compound and the active ionic liquid, must be established. This can be achieved for example by destroying the membrane or foil or other means separating the first compartment and the second compartment of the reaction chamber, or by destroying the receptacle containing one of the essential constituents of the composition for generating oxygen. The membrane or other separating means may be, for example, destroyed by a cutting edge of a cutting device arranged in one of the compartments of the reaction chamber, and the receptacle arranged within a reaction chamber containing only one compartment may be, for example, destroyed by a solid plate or a grid. Both the cutting device having the cutting edge and the solid plate or grid are moved upon activation by an actuator, for example a spring mechanism. The actuator may be actuated, for example, by a person requiring oxygen or may be actuated automatically, once a low oxygen condition is sensed by an oxygen sensor.

Once contact of the constituents has been established, oxygen generation begins promptly or somewhat delayed, depending on the state of the constituents as will be described below. The oxygen leaves the reaction chamber via means allowing the passage of oxygen, while otherwise sealing the reaction chamber, for example a gas permeable membrane or any other structure which is gas permeable, but liquid tight, e.g. a frit or a molecular sieve. When the reaction chamber is arranged within a container, the oxygen may be released into a head space of the container, and leave the container through an oxygen outlet.

In an exemplary embodiment, the device for generating oxygen comprises more than one reaction chamber, and the at least two reaction chambers are arranged within a common container. Each reaction chamber may be provided, individually, with means for establishing physical contact of the constituents of the composition for generating oxygen, or alternatively, a common such means may be provided for a plurality of the reaction chambers or for all reaction chambers. The oxygen generated in each reaction chamber is released into a common head space of the container, and leaves the container through an oxygen outlet.

The embodiment comprising a plurality of reaction chambers allows that oxygen can be provided over a particularly long time period by charging the reaction chambers with compositions for generating oxygen having different oxygen release profiles. In principle, such composition having different oxygen release profiles may be also charged into one single reaction chamber, thus providing oxygen over a long time period. It is readily apparent that such device for generating oxygen having only one reaction chamber is of a very simple construction. Simple constructions are typically the most reliable ones.

It has been found by the present inventors, that the course of the decomposition reaction of the peroxide compound can be influenced by various factors.

The nature of the peroxide compound has no or almost no influence, i.e. all tested peroxide compounds have been found to behave equivalently.

As regards the active ionic liquid, the activity can be manipulated by varying either the cation or the anion or both. As a cation, different heterocycles can be used, and the heterocycles can be substituted with different substituents. As regards the anion, different metals can be used, and the halides or pseudohalides coordinating to the transition metal or other metal can be also varied. All these modifications have some influence on the peroxide decomposition rate and on the time point of onset of the decomposition reaction. Also the maximum reaction temperature reached during the decomposition reaction is somewhat different for different chemical compositions of the ionic liquid. The maximum reaction temperature, however, also depends on the amount of the active ionic liquid and, in particular, on the amount of the peroxide compound used. The reaction temperature increases with increasing amount of peroxide, but it never exceeds about 120° C.

The greatest influence on the decomposition reaction profile was found for the surface area of the peroxide compound exposed to the active ionic liquid. In the examples below, hydrogen peroxide adduct compounds have been used. It is evident that the reaction rate can be considerably varied by reducing or enlarging the surface area of the hydrogen peroxide adduct compound. The decomposition reaction is particularly fast, when the peroxo compounds are present in the form of fine particles. Small particles can be easily and quickly accessed by the active ionic liquid.

The surface area of the hydrogen peroxide adduct compound or of any other solid peroxide compound which is readily accessible by the active ionic liquid can be effectively reduced by pressing the peroxide into powder compacts, e.g. pellets. Powder compacts may differ in shape (having, for example, cylindrical or rectangular block shapes), in dimensions, in degree of compacting (which increases with increasing compacting pressure), and in weight. It has been found that the weight directly influences the amount of oxygen generated, i.e. the reaction is scalable. The amount of peroxide in the reaction mixture determines the amount of oxygen generated. The reaction rate, however, is independent of the weight and the shape of the powder compacts, and also quite independent of the dimensions of the powder compacts.

A strong influence has been found for the degree of compaction. High compaction pressures clearly delayed the onset of the reaction and/or extended the time period of oxygen generation. The reason is that high compaction pressure results in high density of the powder compacts, resulting in low porosity of the powder compacts. Powder compacts having many open pores at the surfaces thereof can be easily and quickly penetrated by the ionic liquid, while powder compacts having only few open pores at the surfaces thereof do not allow fast penetration of the ionic liquid into the bulk of the powder compact. Therefore, contact with the active ionic liquid is delayed in the case of powder compacts having a high degree of compaction, and the delay increases with increasing degree of compaction. Interestingly, the particle size of the peroxide before compaction does not influence the delay of the reaction onset.

As a consequence, compressing the peroxide compound is the measure of choice for manipulating the time period, when oxygen generation occurs. As a rule of thumb it can be said that the delay in the onset of the decomposition reaction increases with increasing compaction pressure.

It will be appreciated that the disclosed uses, methods and devices may take advantage of any of the materials described above in relation to the compositions and products and vice versa.

All references herein to "comprising" should be understood to encompass "including" and "containing" as well as "consisting of" and "consisting essentially of".

The term "a" means "at least one".

BRIEF DESCRIPTION OF THE DRAWINGS

The invention will be further illustrated by the following non limiting examples with reference to the accompanying drawings, wherein.

DETAILED DESCRIPTION

In all graphs illustrating oxygen evolution or reaction temperature, oxygen evolution (or reaction temperature, respectively) is plotted against runtime, wherein runtime is the time which starts running at the time point of contacting the oxygen source and the ionic liquid.

In the following examples, a drum gas meter having a simple voltage pick-up, and an analog-digital-converter was used for measuring the oxygen volume which was generated by the peroxide decomposition reaction. This resulted in a systematic measurement error. In many examples, the gas volume which was measured, was somewhat higher than the theoretically possible gas volume. The reason is that the decomposition reaction is slightly exothermic, somewhat heating up the oxygen generated to a temperature somewhat above room temperature. When the oxygen exits the reaction chamber, it is cooled down to room temperature, leading to contraction of the gas volume. The drum gas meter used could not compensate the volume errors due to contraction of the gas volume upon cooling down. Rather, the negative volume (volume decrease) was registered as a positive volume (volume increase). The value of 0.13×1000 cm3 indicated in some of the Figures corresponds to the theoretical amount of releasable O2.

In the examples, the following abbreviations are used

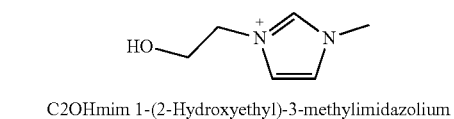

C2OHmim 1-(2-Hydroxyethyl)-3-methylimidazolium

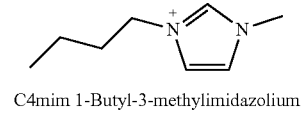

C4mim 1-Butyl-3-methylimidazolium

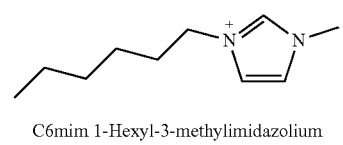

C6mim 1-Hexyl-3-methylimidazolium

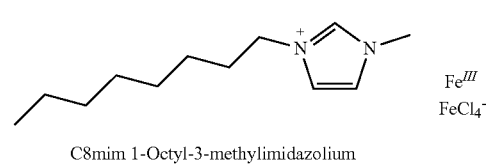

C8mim 1-Octyl-3-methylimidazolium

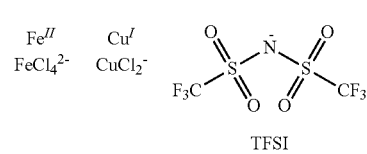

TFSI

UHP: urea hydrogen peroxide
IL: ionic liquid

Example 1

10.0 mmol urea hydrogen peroxide (UHP) and 10.0 mmol of different imidazolium tetrachloroferrates are charged into a round bottom flask. After closing the vessel, the oxygen volume released is measured with a drum gas meter. Charged amounts and volume of gases released are indicated for different active ionic liquids in table 1.

TABLE 1

Charged amounts and volume of oxygen released for reactions of different imidazolium tetrachlorferrates and 1 g UHP.

| ionic liquid | C$_2$OHmimFeCl$_4$ | C$_4$mimFeCl$_4$ | C$_6$mimFeCl$_4$ | C$_8$mimFeCl$_4$ |
|---|---|---|---|---|
| mass UHP | 1 g | 1 g | 1 g | 1 g |
| mass IL | 3.10 g | 3.36 g | 3.65 g | 3.93 g |
| gas volume | 132.5 cm$^3$ | 135 cm$^3$ | 135 cm$^3$ | 165 cm$^3$ |

Figure 1:
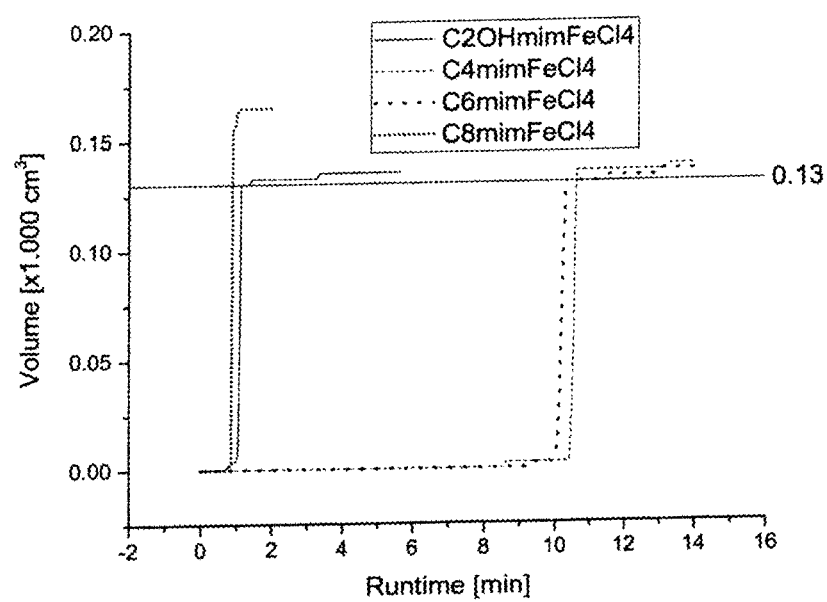
FIGS. 1 to 3 are graphs illustrating oxygen evolution from UHP with different ionic liquid formulations.

The reaction profile is shown in FIG. 1. FIG. 1 shows that the onset of the decomposition reaction strongly depends on the particular ionic liquid used.

Example 2

10.0 mmol urea hydrogen peroxide (UHP) each are charged into a vessel together with ionic liquid formulations as indicated in table 2. After closing the vessel, the gas volume released is measured. The results are illustrated in table 2 and FIG. 2.

TABLE 2

| IL-formulation | $C_4mimCuCl_2$ | 6% solution of $C_4mimCuCl_2$ in $C_4mimTFSI$ | $C_6mim_2Fe(II)Cl_4$ | $C_4mimFe(III)Cl_4$:$C_6mim_2Fe(II)Cl_4$ 1:1 (molar) |
|---|---|---|---|---|
| amount UHP | 1 g | 1 g | 1 g | 1 g |
| amount IL | 2.73 g | 2.69 g | 5.32 g | 4.34 g |
| gas volume | 150 cm$^3$ | 113 cm$^3$ | 120 cm$^3$ | 108 cm$^3$ |

Charged amounts and volumes of gases released for reactions of different ionic liquid formulations with 1 g UHP.

Figure 2:
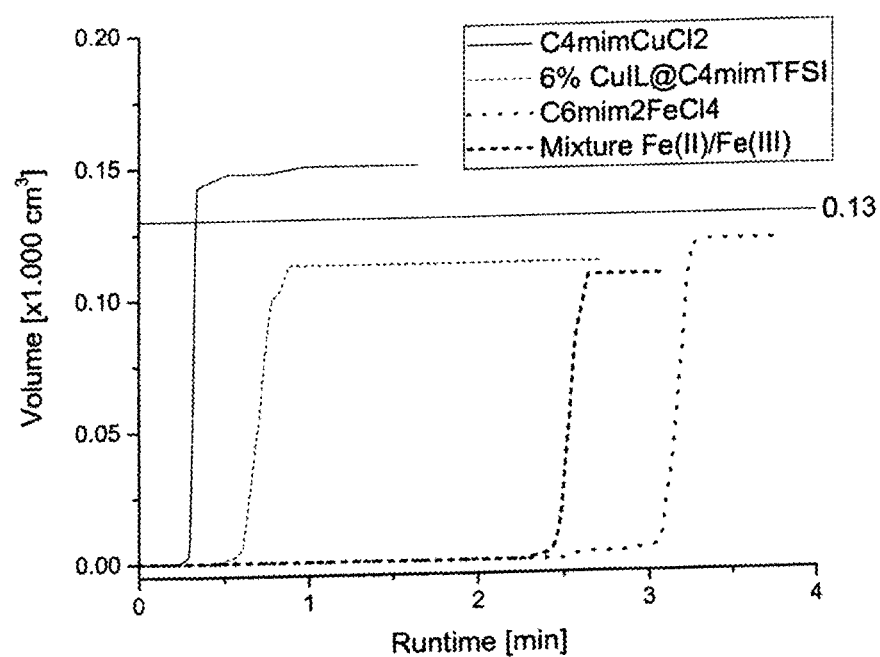

Table 2 and FIG. 2 show that the amounts of oxygen released are similar for different ionic liquids, however, the onset of the decomposition reaction varies considerably for different ionic liquid formulations.

Example 3

10 mmol UHP and 10 mmol of different imidazolium tetrahaloferrates are charged into a round bottom flask. The particular ionic liquids used are indicated in table 3. After closing the vessel, the gas volume released were measured with a drum gas meter. Charged amounts and volumes of gases released by the different ionic liquids are also indicated in table 3.

TABLE 3

| IL formulation | $C_4mimFeBr_4$ | $C_4mimFeBrCl_3$ | $C_4mimFeCl_4$ |
|---|---|---|---|
| amount UHP | 1 g | 1 g | 1 g |
| amount IL | 5.15 g | 3.81 g | 3.36 g |
| gas volume | 128 cm$^3$ | 128 cm$^3$ | 135 cm$^3$ |

Charged amounts and gas volumes released for reactions of different imidazolium tetrahaloferrates and 1 g UHP.

Figure 3:
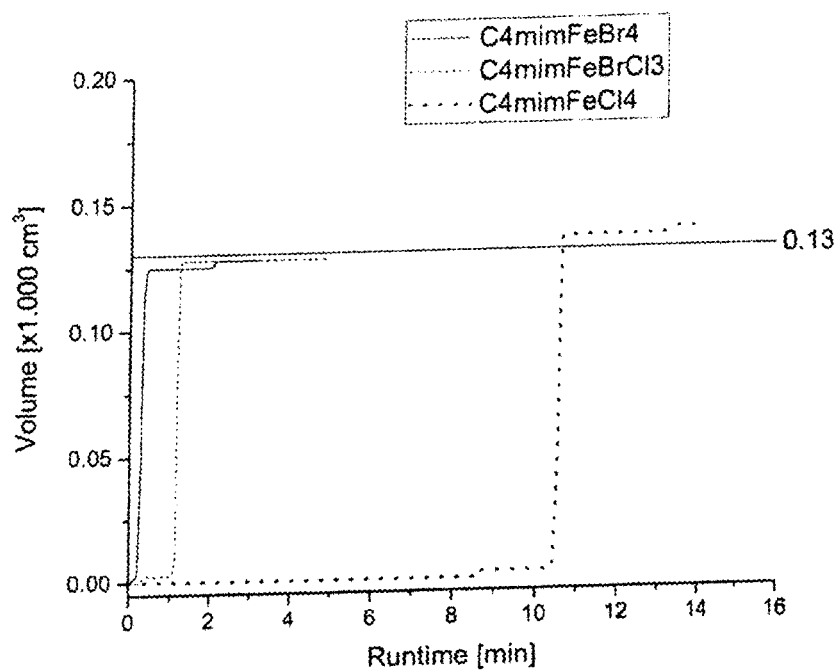

As table 3 and FIG. 3 show, the oxygen volumes released are very similar for the different tetrahaloferrates, however, the time point of onset of the decomposition reaction differs considerably for the different tetrahaloferrates.

Example 4

Figure 4:
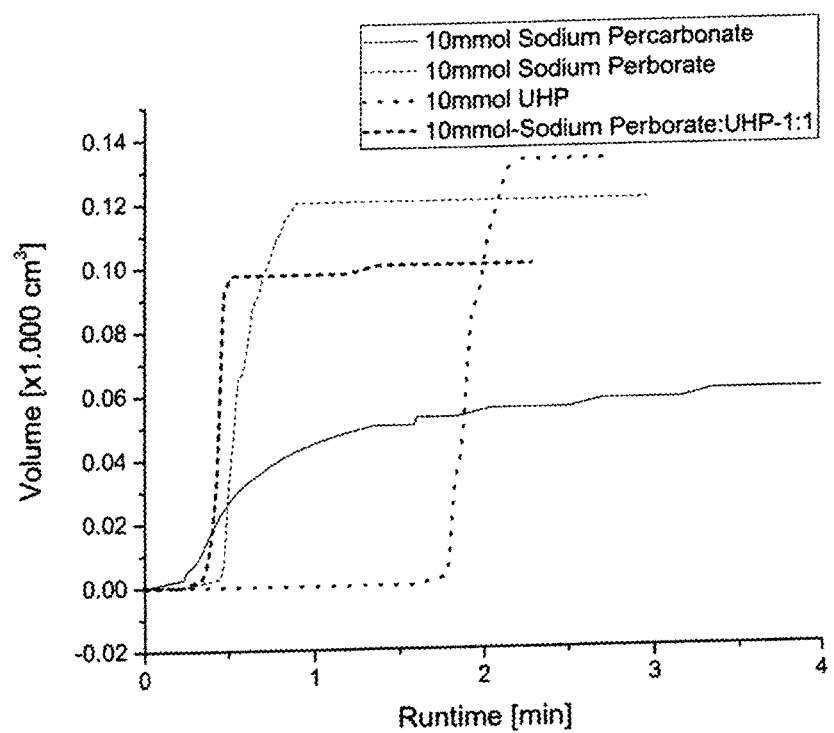
FIG. 4 is a graph illustrating oxygen evolution from different peroxide compounds with C4mimFeCl4.

10 mmol hydrogen peroxide adduct compounds as indicated in table 4 and 10 mmol $C_4mim$ Fe Cl4 are charged into a round bottom flask. After closing the vessel, the gas volume released is measured with a drum gas meter. Charged amounts and volumes of oxygen released from different peroxides are shown in table 4 and FIG. 4.

It can be seen that different peroxide compounds, and also mixtures of peroxide compounds, are effective for producing oxygen.

TABLE 4

| peroxide adduct | sodiumpercarbonate | sodiumperborate | UHP | sodiumperborate:UHP 1:1 (molar) |
|---|---|---|---|---|
| amount peroxide | 1.5 g | 1.54 g | 1 g | 1.25 g |
| amount IL | 3.36 g | 3.36 g | 3.36 g | 3.36 g |
| gas volume | 128 cm$^3$ | 128 cm$^3$ | 133 cm$^3$ | 135 cm$^3$ |

Example 5

10 mmol UHP and 10 mmol active ionic liquid as indicated in table 5 are charged into a round bottom flask. After closing the vessel the oxygen volume released is measured by a drum gas meter. Simultaneously, the temperature of the reaction solution is measured with a thermocouple (K-type). The maximum temperatures measured are listed in table 5 and shown in FIG. 5. It can be seen that the peak temperatures are different for different ionic liquids, however, peak temperatures are always low. Even the highest peak temperature is below 120° C.

TABLE 5

Maximum reaction temperature for different ionic liquids when decomposing 1 g UHP

| IL | maximum temperature |
|---|---|
| $C_2OHmimFeCl_4$ | 79° C. |
| $C_4mimCuCl_2$ | 81° C. |
| $C_4imFeBr_4$ | 119° C. |
| $C_4mimFeCl_4$ | 57° C. |

Example 6

Different amounts of urea hydrogenperoxide (UHP) and equimolar amounts of C4mim Fe Cl$_4$ are charged into a round bottom flask. After closing the vessel, the gas volume released is measured with a drum gas meter, and simultaneously the temperature in the reaction solution is measured with a thermocouple (K-type). The maximum temperatures measured and the volumes of gas released are listed in table 6. The maximum temperatures are also shown FIG. 6.

TABLE 6

| amount UHP | gas volume released | maximum temperature |
|---|---|---|
| 1 g UHP | 140 cm$^3$ | 79° C. |
| 5 g UHP | 545 cm$^3$ | 81° C. |
| 10 g UHP | 1388 cm$^3$ | 119° C. |

Maximum reaction temperature for different ionic liquids when decomposing 1 g UHP.

Figure 6:
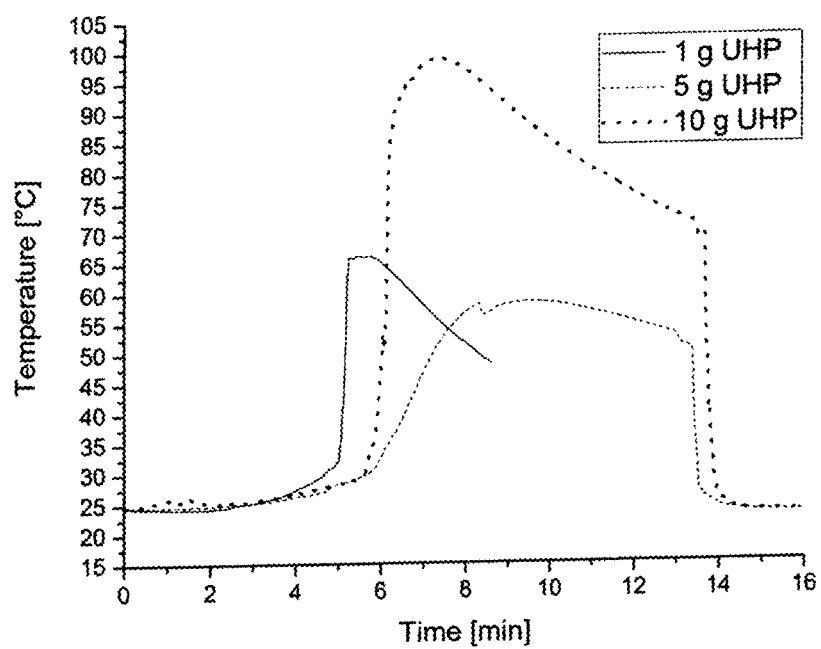
FIG. 6 is a graph illustrating reaction temperatures during decomposition of different amounts of UHP.

As table 6 and FIG. 6 show, the maximum temperatures increase with increasing amounts of peroxide. However, in all cases, the reaction temperatures are below 120° C.

Example 7

Figure 7:
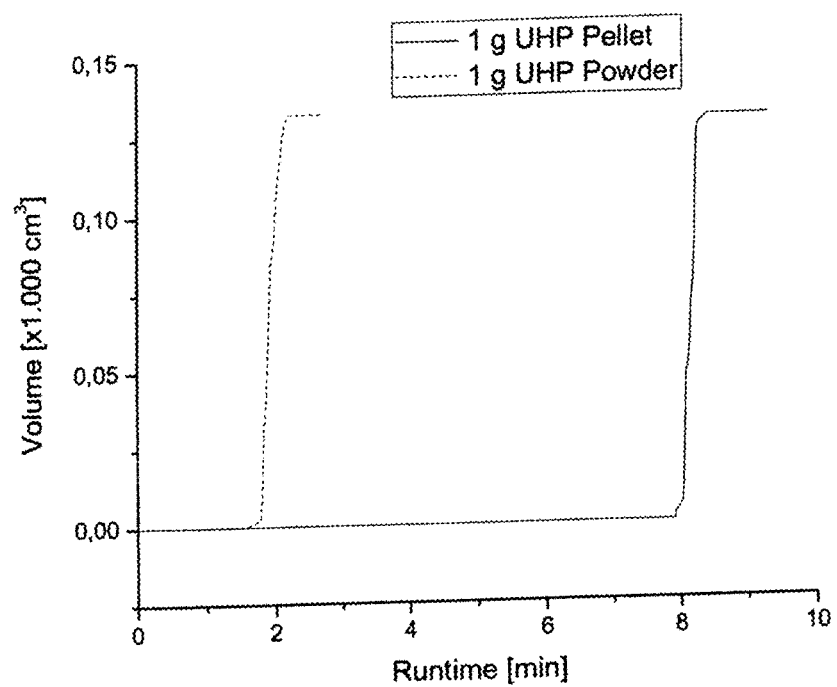
FIG. 7 is a graph illustrating oxygen evolution from powder compacts as compared to powder.

1 g urea hydrogen peroxide adduct compound (UHP) in powder form or compressed into a pellet (cylindrical mold) or compressed into a cube, was added in a glass flask with an imidazoliumferrat-based ionic liquid formulation (C4mimFeCl4) having peroxide decomposing capability. After closing the reaction vessel, the oxygen volume released is measured with a drum gas meter. Compression pressures, oxygen released and time till complete release of the available oxygen are listed in table 7. FIG. 7 depicts the oxygen volume released versus reaction time for the UHP powder compacts (pellets) and the UHP powder.

Figure 8:
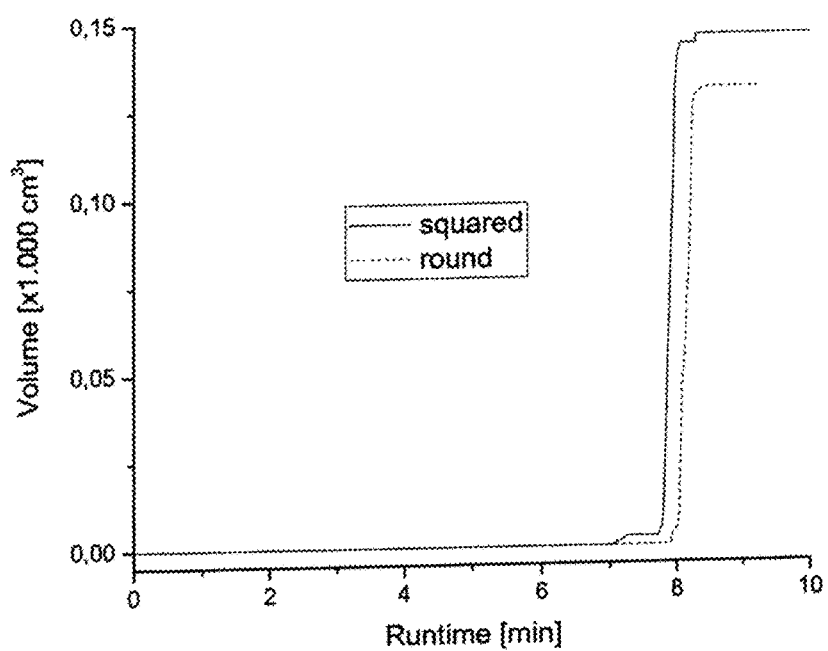
FIG. 8 is a graph illustrating oxygen evolution from different amounts of peroxide compacts, having different weight at an equivalent compaction pressure.

The results clearly prove that in the case of an oxygen source in powder form, the decomposition reaction of the oxygen source starts quite promptly after combining the oxygen source and the active ionic liquid, whereas in the case of an oxygen source in compressed form, the onset of the decomposition reaction is somewhat delayed. FIG. 8 illustrates a comparison of the oxygen evolution of different mold geometries for peroxide powder compacts of identical compression.

FIG. 8 compares the decomposition reaction profiles of squared powder compacts and round powder compacts. The powder compacts have the same degree of compression. Obviously, the different geometries do not influence the decomposition reaction profile. Rather reaction rate on onset of the reaction, and volume of oxygen released are very similar for the squared and the round powder compact.

TABLE 7

| peroxide adduct (shape) | mass | compaction pressure | volume | time1 |
|---|---|---|---|---|
| UHP (powder) | 1 g | — | 133 cm$^3$ | 2.2 min |
| UHP (pellet) | 1 g | 75 MPa | 135 cm$^3$ | 8.4 min |
| UHP (squared) | 1 g | 74 MPa | 142 cm$^3$ | 8.1 min |

1"time" means time till complete release of all available oxygen.

Example 8

Figure 9:
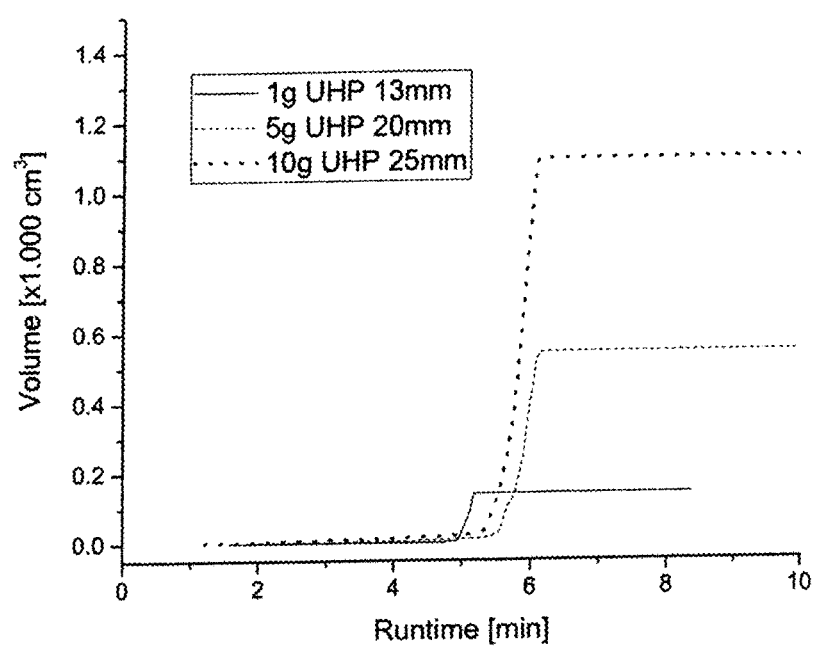
FIG. 9 is a graph illustrating oxygen evolution from peroxide powder compacts having different shapes.
Figure 10:
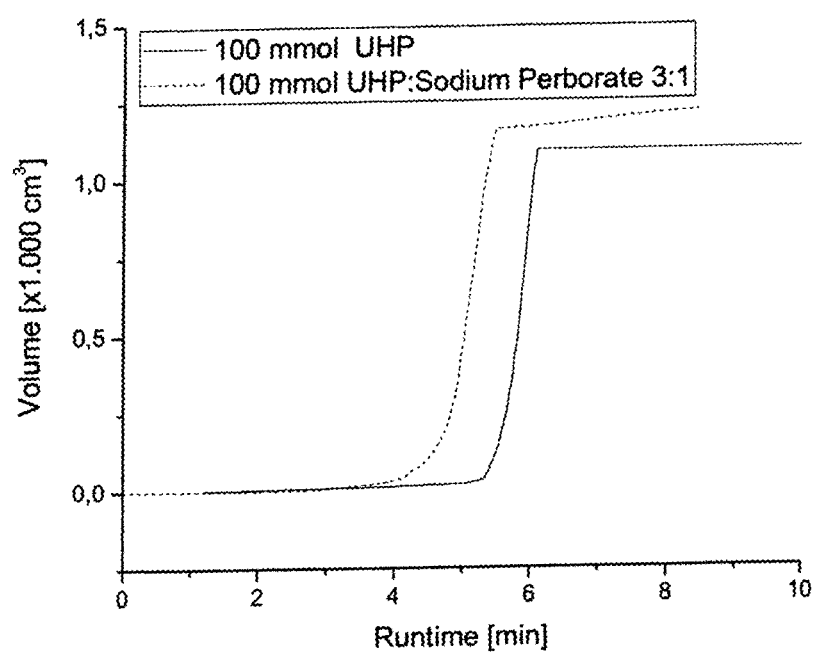
FIG. 10 is a graph illustrating oxygen evolution from different peroxide compounds.

Different amounts of urea hydrogen peroxide compound compressed into pellets (round shape) were admixed in a glass flask with an imidazoliumferrate based ionic liquid formulation (C4mim Fe C14) having peroxide decomposing capability. After closing the reaction vessel, the gas volume released is measured with a drum gas meter. Likewise, an oxygen source, composed of UHP and sodium perborate (molar ratio 1:3) was treated in the same manner. Peroxide amounts, compaction pressure, volume of gas released, and time till complete release of the available oxygen are listed in table 8. Oxygen generation for the urea hydrogen peroxide pellets (the pellets having different diameters due to different amounts of UHP) versus reaction time is depicted in FIG. 9. FIG. 10 depicts oxygen generation from pellets of mixed peroxide adduct (UHP: sodium perborate, molar ratio 1:3).

TABLE 8

| peroxide adduct (shape) | mass | compaction pressure | volume | time[1] |
|---|---|---|---|---|
| UHP (Pellet) | 1 g | 75 MPa | 140 cm$^3$ | 5.5 min |
| UHP (Pellet) | 5 g | 75 MPa | 550 cm$^3$ | 6.1 min |
| UHP (Pellet) | 10 g | 75 MPa | 1100 cm$^3$ | 6.1 min |
| UHP:Sodium perborate 1:3 (molar) (pellet) | 10.9 g | 75 MPa | 1165 cm$^3$ | 5.5 min |

[1]"time" means time till complete release of all available oxygen

Figure 11:
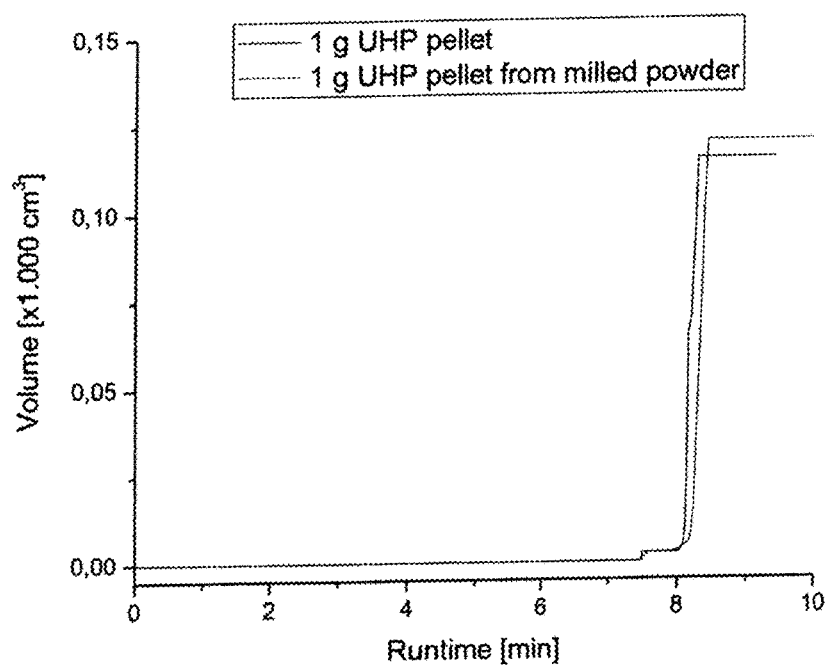
FIG. 11 is a graph illustrating oxygen evolution from peroxide powder compounds having different particle sizes before compacting, FIGS. 12 to 16 schematically illustrate several embodiments of devices for generating oxygen from compositions according to this invention.

FIG. 11 depicts a comparison of the oxygen release from the pellet having a mass of 1 g, comparing pellets made from UHP powder with different particle sizes.

It can be seen from FIG. 9 that the amount of peroxide used determines the amount of oxygen generated. The reaction rate and the time of onset of the decomposition reaction are not significantly influenced by the amount of the peroxide used.

FIG. 10 illustrates that the oxygen generation from urea hydrogen peroxide as the sole oxygen source is similar to the oxygen generation from a mixed oxygen source comprising UHP and sodium perborate. The particular oxygen source has little influence on the amount of oxygen generated, the reaction rate, and the onset of the decomposition reaction.

While the degree of compaction, i.e. the compaction pressure, significantly influences the time point of the onset of the decomposition reaction, particle sizes before compaction do not play a role. This is evident from FIG. 11, comparing oxygen generation from UHP pellets of equal weight, which had been pressed with the same compaction pressure. One example, however, had been milled into very fine particles before compression. Nevertheless, the reaction profile is nearly identical for both samples.

In exemplary embodiments, a device for generating oxygen from compositions as described above which uses ionic liquids having metallate anions for decomposing a peroxide compound as an oxygen source, and for dissipating reaction heat generated during the decomposition reaction, is specifically designed. A device for generating oxygen, in exemplary embodiments, has at least one reaction chamber for storing the composition in a condition where the oxygen source and the active ionic liquid are not in physical contact with each other. Such physical contact of the oxygen source and the active ionic liquid must be established at the very moment when oxygen is required. In exemplary embodiments, the device is equipped with suitable means for allowing the oxygen source and the active ionic liquid to contact each other at that very moment. Furthermore, in exemplary embodiments the device allows that the generated oxygen exits the reaction chamber. Some exemplary devices are illustrated in FIGS. 12 to 16, wherein like reference numerals designate like components. The description of such exemplary embodiments shall not be construed as limiting the invention in any manner.

Figure 12:
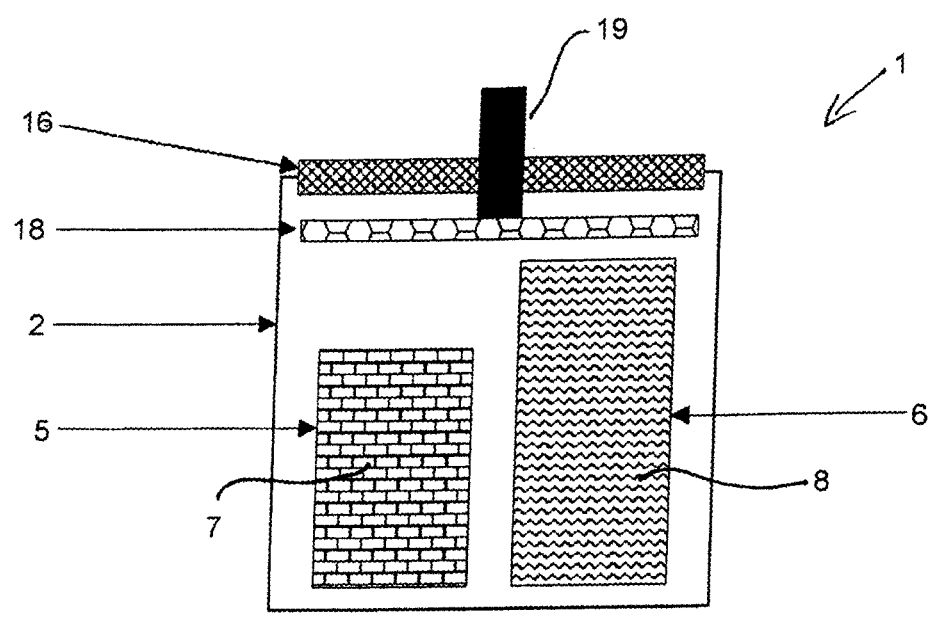

FIG. 12 illustrates a device 1 for generating oxygen having one single reaction chamber 2 for storing the composition for generating oxygen. In such a single reaction chamber 2 at least one of the oxygen source and the active ionic liquid is enclosed in a receptacle in order to avoid contact with the respective other constituent contained in the reaction chamber 2. In the embodiment shown in FIG. 12, two receptacles 5, 6 are arranged in the reaction chamber. Receptacle 5 contains the oxygen source formulation 7, for example in powder form or compressed into pellets. Receptacle 6 contains an ionic liquid formulation 8. Alternatively, there may be only one receptacle for enclosing the oxygen source formulation, while the ionic liquid formulation is "free" within reaction chamber 2, or ionic liquid formulation 8 may be enclosed within a receptacle, while the oxygen source formulation 7 is not enclosed in a separate receptacle.

Herein, the term "oxygen source formulation" means that the oxygen source may be one single peroxide compound, but may be as well a combination of two or more peroxide compounds, and may optionally contain any additives not detrimentally interacting with the peroxide decomposition reaction.

The term "ionic liquid formulation" as used herein indicates that the ionic liquid may be one single active ionic liquid as described above, but may be as well a combination of two or more active ionic liquids as described above, or may be diluted by one or several different non active ionic liquids. Furthermore, the ionic liquid formulation may contain any additives not detrimentally interacting with the peroxide decomposition reaction.

It is desirable to store the oxygen source formulation 7 and the ionic liquid formulation 8 within the reaction chamber 2 in such an arrangement that the oxygen source formulation and the ionic liquid formulation will be able to get intimately mixed once oxygen generations is required. On the other hand, untimely mixing shall be avoided. Therefore, in the exemplary embodiments both the oxygen source formulation and the ionic liquid formulation are placed in a receptacle each. This constitutes an advantageous precautionary measure against accidental mixing of the oxygen source and the active ionic liquid in case of receptacle leakage or breakage.

In a situation where oxygen shall be generated, receptacle 5, or receptacles 5 and 6, respectively, are destroyed by a breaking device 18. In FIG. 12, breaking device 18 has the form of a plate, however, means for destroying the receptacle(s) are not limited to plates, and other means are known to persons skilled in the art, for example firing pins or grids. Movement of plate 18 can be achieved by a spring 19 or another activation mechanism. During storage of the device for generating oxygen, spring 19 is under tension and holds plate 18 at a position distant from receptacles 5, 6. Once the tension is released by a suitable trigger mechanism (not shown), spring 19 moves plate 18 towards receptacles 5, 6, and plate 18 destroys receptacles 5, 6. Such a trigger may be, for example, pulling an oxygen mask towards a passenger in an air plane. Another exemplary trigger mechanism is an oxygen sensor sensing a low oxygen condition.

Receptacles 5, 6, and plate 18 are made from materials which guarantee that receptacles 5, 6 will be broken or ruptured when hit by plate 18. Exemplary materials are plastic foils or glass for receptacles 5, 6, and thicker plastic material or metal for plate 18.

Destruction of receptacles 5, 6 causes mixing of the oxygen source formulation 7 and the ionic liquid formulation 8, and initiates oxygen generation already at room temperature or temperatures below room temperature. In order to allow that the oxygen exits reaction chamber 2, reaction chamber 2 has an opening which is sealed, in the illustrated embodiment, with a gas permeable membrane 16. The opening may be at a different position than shown in FIG. 12, or there may be more than one opening. This applies analogously to all devices for generating oxygen of this invention.

The oxygen generated in the devices of this invention may be passed through a filter or other purification means as known in the art. The devices may be equipped with such means.

The oxygen generating reaction is an only slightly exothermic process, and reaction heat generated by the decomposition process does not considerably heat up the oxygen generated. Oxygen exiting the reaction chamber is nearly at a temperature suitable for breathing, i.e. well below 150° C. Reaction chamber 2 does not need to resist high temperatures, and maybe made from lightweight, low melting materials such as plastic. In addition, any bulky insulation is not required. This is particularly advantageous in all cases where weight must be saved and/or space is limited, for example in the case of oxygen masks which shall be installed in an aircraft.

Figure 13:
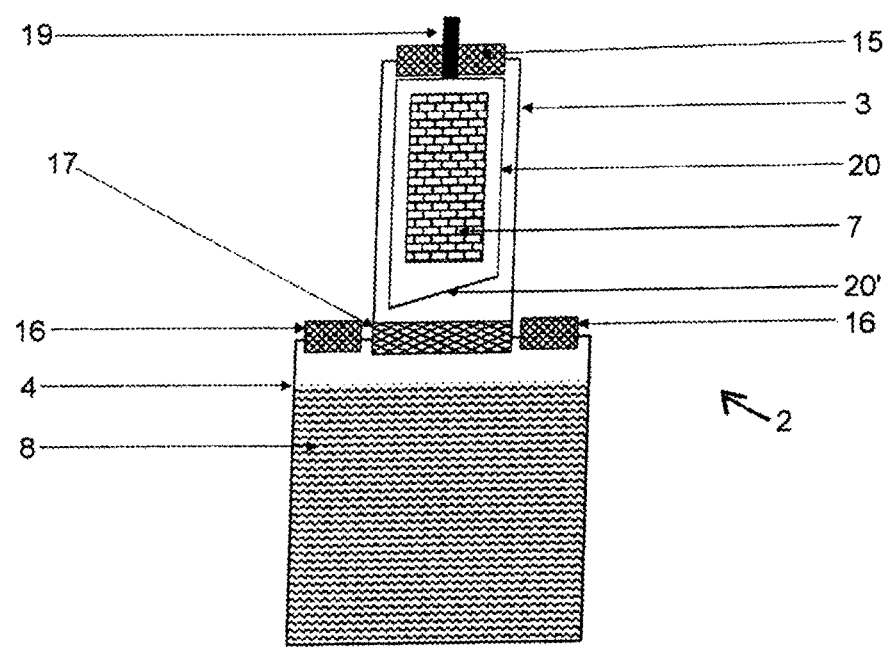

FIG. 13 illustrates an alternative embodiment of an inventive device 1 for generating oxygen. In the embodiment of FIG. 13, the reaction chamber 2 has two compartments, a first compartment 3 and a second compartment 4, which are separated by a liquid tight membrane 17. The first compartment 3 contains the oxygen source formulation 7, and is equipped with a cutting device 20 having a cutting edge 20'. The cutting device is arranged in a position that allows cutting edge 20' to cut through membrane 17 separating the first compartment 3 and the second compartment 4.

Compartments 3, 4 have openings sealed by membranes 15, 16, respectively. Membranes 15, 16 are gas permeable, thus allowing the oxygen generated during the oxygen generating reaction to exit reaction chamber 2.

An activation mechanism 19, for example a spring, is provided for moving cutting edge 20' towards membrane 17, and through membrane 17. Such a mechanism is described in DE 10 2009 041 065 A1. As explained in connection with FIG. 12, spring 19 is under tension during storage of device 1, and once the tension is released by a trigger mechanism (not shown), spring 19 moves the cutting device towards membrane 17, cutting edge 20' destroys membrane 17, and first compartment 3 and second compartment 4 are combined into one single reaction chamber 2.

In the embodiment illustrated in FIG. 13, oxygen source formulation 7 is contained in the first compartment 3, and ionic liquid formulation 8 is contained in second compartment 4. Upon destruction of membrane 17, oxygen source formulation 7 drops into second compartment 4, and mixes with ionic liquid formulation 8. The oxygen generated exits the reaction chamber 2 through membranes 15, 16.

Of course, it is also possible to place ionic liquid formulation 8 into the first compartment 3 and oxygen source formulation 7 into the second compartment 4.

As a material for cutting device 20, any material may be used which may cut membrane 17, for example a metal sheet. The first compartment 3 and the second compartment 4 can be formed from the same materials as the single reaction chamber 2 illustrated in FIG. 12.

Figure 14:
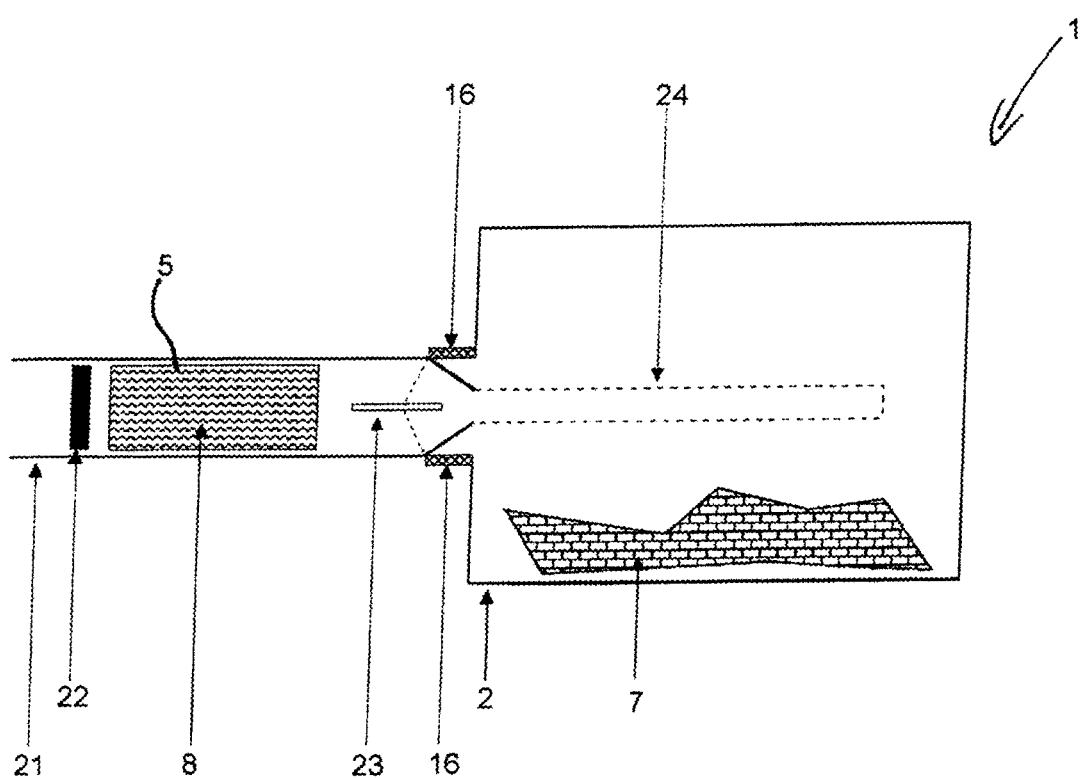

Another embodiment of an inventive device 1 for generating oxygen is illustrated in FIG. 14. In the embodiment of FIG. 14, reaction chamber 2 is equipped with an injection device 21, for example a syringe, or another dosing device.

Reaction chamber 2 and injection device 21 are connected, or constitute separate units which can be connected to form one single unit. An opening, or several openings, in the wall of reaction chamber 2 allow that oxygen generated during the peroxide decomposition reaction exits reaction chamber 2. The openings are sealed, in the illustrated embodiment, by gas permeable membranes 16. In the embodiment illustrated in FIG. 14, the openings are provided at the junction of reaction chamber 2 and injection device 21.

The exemplary injection device of FIG. 14 comprises a slide bar 22, a spike 23, and an injection lance 24. The injection device is adapted for holding the oxygen source formulation 7 or the ionic liquid formulation 8, in the illustrated example the ionic liquid formulation 8. Ionic liquid formulation 8 is contained in a receptacle 5, made from a material which can be easily ruptured, for example a plastic foil. Oxygen source formulation 7 is contained in reaction chamber 2.

Slide bar 22 can be actuated in an analogous manner as the breaking device 18 in FIG. 12, and the cutting device 20 in FIG. 13. Once actuated, slide bar 22 pushes receptacle 5 towards spike 23, receptacle 5 is ruptured, and ionic liquid formulation 8 is injected through injection lance 24 into reaction chamber 2. Preferably, injection lance 24 is provided with several holes (not shown) in order to provide uniform distribution of ionic liquid formulation 8. Ionic liquid formulation 8 soaks oxygen source formulation 7, and the peroxide decomposition reaction starts, generating oxygen. The oxygen leaves reaction chamber 2 via membranes 16.

Analogously to the embodiments described above, the arrangement of oxygen source formulation 7 and ionic liquid formulation 8 may be different from the arrangement illustrated in FIG. 14. In particular, if not a liquid, but solid matter is contained in the injection device or dosing unit 21, no receptacle 5 is required, and means for destroying the receptacle, such as spike 23, and an injection lance are also not required.

Figure 15:
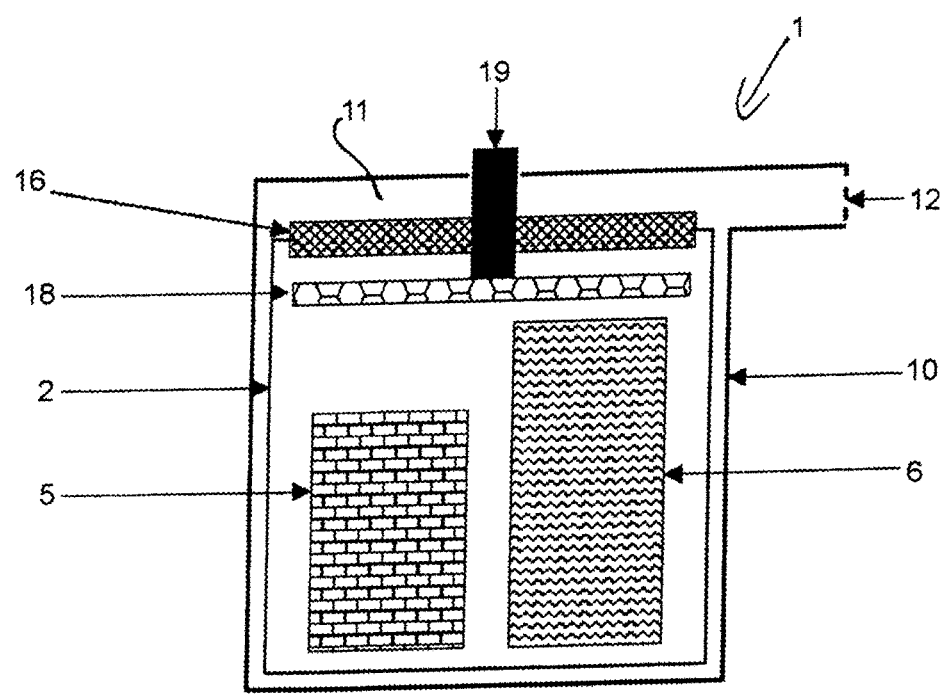

FIG. 15 depicts an embodiment of the device 1 for generating oxygen which is similar to the embodiment depicted in FIG. 12. Different from the embodiment of FIG. 12, the device for generating oxygen of FIG. 15 is contained in a container 10 surrounding and protecting reaction chamber 2. In this case, the oxygen generated is not directly released into the environment, but rather enters into a gas space 11 between gas permeable membrane 16 and an upper wall of container 10. The oxygen exits gas space 11 via a gas outlet 12 which may be, for example, provided with a filter.

A device 1 as shown in FIG. 15 typically does not need any further thermal insulation. Rather, container 10 provides for sufficient insulation. If desired, a thin layer (for example, having a thickness of about 1 to 3 mm) of an insulating material may be placed between the outer wall of reaction chamber 2 and the inner wall of container 10. Such an insulating material may also serve the additional purpose of holding reaction chamber 2 tightly fixed in place within container 10. No insulating material should be provided between membrane 16 and the container wall opposite to membrane 16, i.e. in gas space 11.

Housing the reaction chamber within a container is particularly advantageous in devices for generating oxygen having more than one reaction chamber, for example two reaction chambers or a plurality or multitude of reaction chambers 2. An embodiment having eight reaction chambers 2 is illustrated in FIG. 16.

Figure 16:
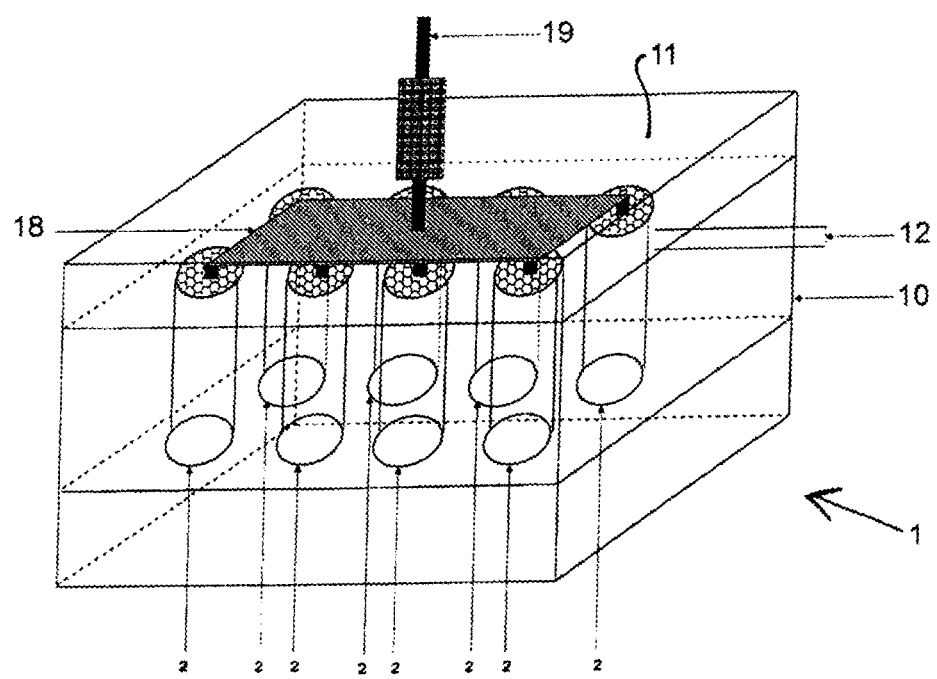

In the device for generating oxygen illustrated in FIG. 16, reaction chambers 2 are shown schematically. Generally, the construction of reaction chambers 2 is not limited in any manner. For example, reaction chambers as illustrated in FIGS. 12 to 14 can be used. Furthermore, the arrangement of the reaction chambers is not limited to the arrangement shown in FIG. 16. Rather, the reaction chambers may be arranged within the container 10 in any appropriate manner.

Oxygen generation within reaction chambers 2 is initiated upon activation of reaction chambers 2. In the embodiment shown in FIG. 16, all reaction chambers 2 are activated simultaneously by a common activation mechanism, such as a spring, designed for pushing a plate 18 towards reaction chambers 2, as described in connection with FIG. 12. Alternatively, each reaction chamber may be activated individually, i.e. may have its own activation mechanism, or several reaction chambers may be arranged to groups, each group having its own activation mechanism. For example, in the embodiment of FIG. 16, the eight reaction chambers might be arranged into two groups of four chambers, each group having its own activation mechanism.

Container 10 provides a gas space 11 receiving oxygen from all reaction chambers 2, and the oxygen collected within gas space 11 exits gas space 11 via gas outlet 12. Alternatively, gas space 11 may be divided into a plurality of compartments. A separate compartment, having its own gas outlet, may be attributed to each reaction chamber 2, or one compartment may provide a common gas space for a group of reaction chambers 2. For example, container 10 may provide two gas spaces 11, and each gas space 11 may collect oxygen from four reaction chambers 2.

A device for generating oxygen having several reaction chambers 2 allows to extend oxygen generation over a long time period. As explained above, the time point of onset of the decomposition reaction can be manipulated by choosing appropriate active ionic liquids and, in particular, by minimising or maximising the accessible surface area of the hydrogen peroxide adduct compound, for example by milling the peroxide compound to a fine powder or by pressing the peroxide compound into powder compacts. The higher the compacting pressure, the higher the density of the resulting powder compacts will be, thus minimising the accessible surface area of the peroxide compound.

In a device as illustrated in FIG. 16, each of the 8 reaction chambers 2 may be charged with a different composition for generating oxygen. For example, four chambers may be charged with the compositions used in example 2, which produce oxygen at four different points in time, a first flush of oxygen being available already 15 seconds after mixing of the oxygen source and the active ionic liquid, and a last flush of oxygen being available about three minutes after mixing of the oxygen source and the active ionic liquid.

The remaining four reaction chambers may be charged with the same composition that provides the last flush of oxygen (three minutes after mixing), however, with oxygen source formulations which have been pressed into powder compacts, the compacting pressure increasing from chamber to chamber. In these chambers, the onset of the decomposition reaction will be further delayed, as compared to the chamber providing a flush of oxygen three minutes after mixing, the delay increasing with increasing compaction pressure. This measure further extends the time span wherein breathable oxygen is available.

Examples 9 and 10 below illustrate oxygen evolution from a device for generating oxygen having nine reaction chambers (example 9), and gas evolution from a device for generating oxygen having 11 reaction chambers as well as the temperature profiles of the 11 reaction chambers (example 10).

Example 9

The ionic liquid formulations listed in table 9 were charged into the reaction chambers of a device for generating oxygen having 9 reaction chambers. Then, each chamber was charged with 10 g urea hydrogen peroxide adduct in pellet form.

Figure 17:
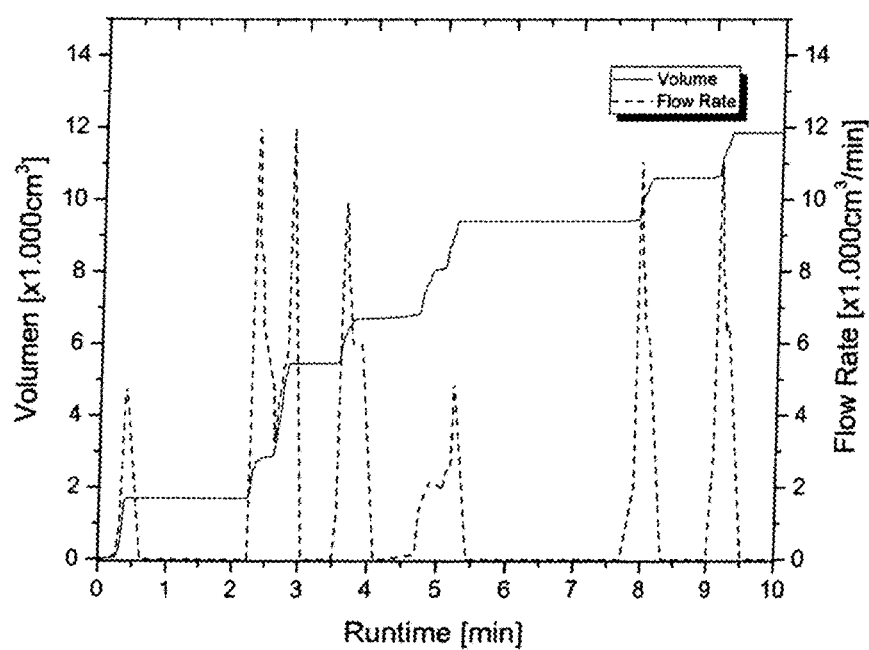
FIGS. 17 and 18 are graphs illustrating oxygen evolution from devices having several reaction chambers.

Oxygen evolution started a few seconds after charging the UHP pellets into the reaction chambers, in a first reaction chamber. After about half a minute, the decomposition reaction was complete in this first reaction chamber, and oxygen evolution stopped. After two minutes, oxygen evolution started in a second reaction chamber, and again the decomposition reaction was completed within about half a minute, but before oxygen evolution stopped completely, the peroxide decomposition reaction started in a third chamber. The remaining chambers followed, the delay in the onset of the decomposition reaction being characteristic for each oxygen generating composition. As a result, the volume of oxygen released increased stepwise (FIG. 17).

TABLE 9

Formulations of the 9 single reactors.

| IL 1 | IL2 | molar ratio IL 1 (mass) | molar ratio IL 2 (mass) |
| --- | --- | --- | --- |
| $C_4mim_2CuCl_4$ | $C_4mimFeCl_4$ | 1 (16.8 g) | 1 (13.7 g) |
| $C_2OHmimFeCl_4$ | $C_4mimFeCl_4$ | 9 (29.2 g) | 1 (3.4 g) |
| $C_2OHmimFeCl_4$ | $C_8mimFeCl_4$ | 3 (24.4 g) | 1 (9.8 g) |
| $C_2OHmimFeCl_4$ | $C_8mimFeCl_4$ | 1 (16.2 g) | 1 (19.6 g) |
| $C_2OHmimFeCl_4$ | $C_6mimFeCl_4$ | 1 (3.2 g) | 9 (32.8 g) |
| $C_2OHmimFeCl_4$ | $C_6mimFeCl_4$ | 1 (2.9 g) | 10 (33.2 g) |
| $C_2OHmimFeCl_4$ | $C_4mimFeCl_4$ | 1 (2.5 g) | 12 (31.1 g) |
| $C_2OHmimFeCl_4$ | $C_4mimFeCl_4$ | 1 (3.3 g) | 9 (30.3 g) |
| $C_2OHmimFeCl_4$ | $C_8mimFeCl_4$ | 1 (8.1 g) | 3 (29.5 g) |

Example 10

Figure 18:
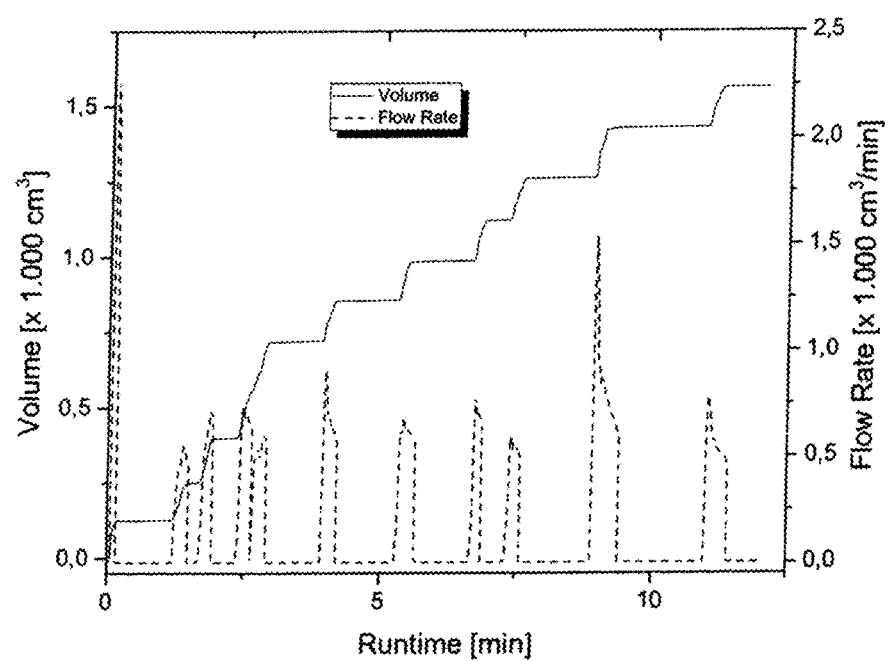
Figure 19:
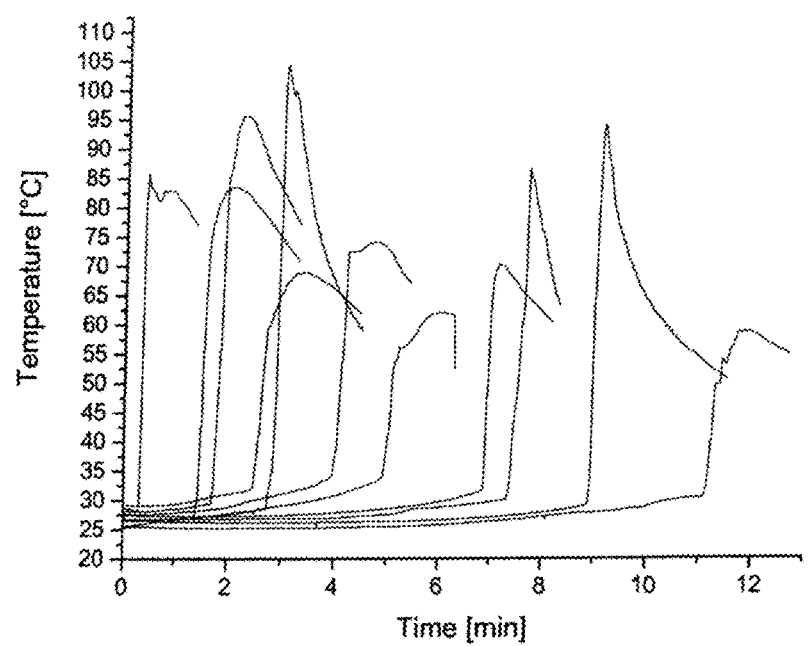
FIG. 19 is a graph illustrating peak reaction temperatures for each reaction chamber of the device illustrated in FIG. 18.

The ionic liquid formulations listed in table 10 below were charged into the individual reaction chambers of a device for generating oxygen having 11 reaction chambers. In addition, 1 g urea hydrogen peroxide adduct in pellet form was charged into each reaction chamber. The oxygen generated was measured with a drum gas meter, and the temperature in each reaction chamber was measured with thermocouples (K-type) provided in each reaction chamber. The results are depicted in FIGS. 18 and 19.

TABLE 10

IL formulations of all 11 reaction chambers

| IL 1 | IL2 | molar ratio IL 1 (mass) | molar ratio IL 2 (mass) |
| --- | --- | --- | --- |
| $C_4mim_2CuCl_4$ | $C_4mimFeCl_4$ | 1 (1.68 g) | 1 (1.37 g) |
| $C_2OHmimFeCl_4$ | $C_4mimFeCl_4$ | 9 (2.92 g) | 1 (0.34 g) |
| $C_2OHmimFeCl_4$ | $C_8mimFeCl_4$ | 3 (2.44 g) | 1 (0.98 g) |
| $C_2OHmimFeCl_4$ | $C_8mimFeCl_4$ | 1 (1.62 g) | 1 (1.96 g) |
| $C_2OHmimFeCl_4$ | $C_6mimFeCl_4$ | 1 (0.32 g) | 9 (3.28 g) |
| $C_2OHmimFeCl_4$ | $C_6mimFeCl_4$ | 1 (1.62 g) | 1 (1.82 g) |
| $C_2OHmimFeCl_4$ | $C_4mimFeCl_4$ | 1 (0.25 g) | 12 (3.11 g) |
| $C_2OHmimFeCl_4$ | $C_8mimFeCl_4$ | 1 (0.81 g) | 3 (2.95 g) |
| $C_2OHmimFeCl_4$ | $C_8mimFeCl_4$ | 1 (0.65 g) | 4 (3.14 g) |
| $C_2OHmimFeCl_4$ | $C_8mimFeCl_4$ | 1 (0.32 g) | 9 (3.54 g) |
| $C_2OHmimFeCl_4$ | $C_8mimFeCl_4$ | 1 (0.30 g) | 10 (3.57 g) |

FIG. 18 shows the oxygen flow rate provided by the 11 reaction chambers, individually, and the volume of oxygen generated versus the run time. Similar to example 9 (FIG. 17) the compositions contained in each reaction chamber generated oxygen for a short time span, with the point in time of onset of the decomposition reaction being characteristic for each oxygen generating composition. The total volume of oxygen generated increased stepwise.

FIG. 19 depicts the temperature profile of each of the 11 individual reaction chambers. FIG. 19 proves that in none of the reaction chambers the maximum reaction temperature exceeded 105° C.

Figure 5:
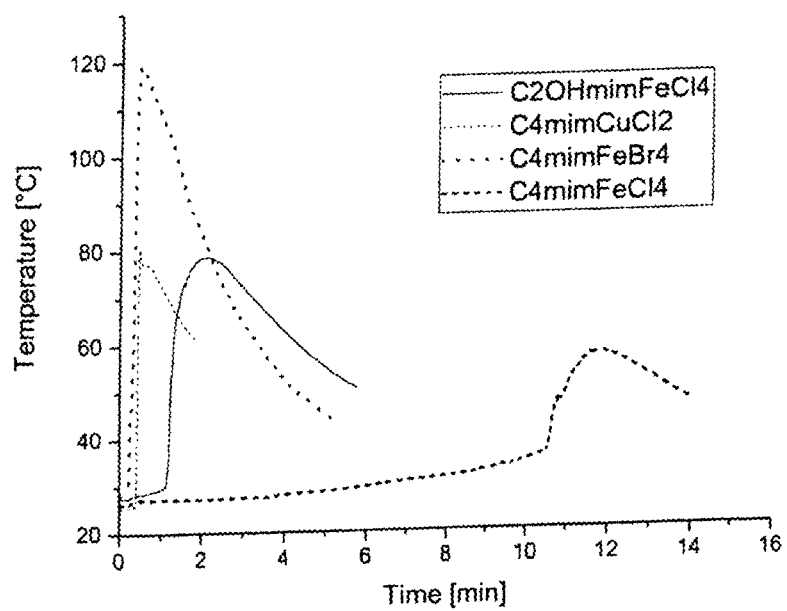
FIG. 5 is a graph illustrating reaction temperatures of reactions of UHP with different ionic liquids.

Reverting again to FIG. 18, it can be seen that breathable oxygen is available for more than 11 minutes, however, the oxygen generation is not as continuous as would be desirable. A smooth oxygen generation can be achieved by providing gas outlet 12 of a device for generating oxygen as illustrated in FIG. 5 with a small orifice or any other means for restricting oxygen flow out of gas space 11.

In each individual reaction chamber, a relatively large amount of oxygen is produced within a short time period. Within this short time period, more oxygen is available than is needed. On the other hand, there are also time periods wherein no oxygen is produced, while oxygen is needed. Consequently, phases of oxygen abundancy and oxygen deficiency alternate with one another. Restricting the outflow of oxygen from gas space 11 provides a buffer which stores excess oxygen for periods of oxygen shortage, thus rendering sufficient oxygen available for a satisfactory long time period.

Since the decomposition reactions are scalable to different reactor sizes, it is easily possible to charge a device for generating oxygen with an oxygen generating composition in a sufficient amount to provide for a desired oxygen flow rate. For emergency systems such desired flow rate is typically at least 4 l oxygen per minute.

The devices for generating oxygen may be designed as disposable devices (for one single use) filled with a composition for generating oxygen, or as reusable devices which can be recharged after use with another composition for generating oxygen. In exemplary embodiments of this invention, oxygen source formulations and ionic liquid formulations are provided in the form of components suitable for recharging a device for generating oxygen, for example in the form of replaceable/mutually interchangeable cartridges. The cartridges are filled with an oxygen source formulation or with an ionic liquid formulation.

The devices for generating oxygen according to the present invention are not sensitive to interruptions of the oxygen production process, in contrast to chlorate candles which can be easily destabilised, for example by shaking. Shaking a device for generating oxygen according to the present invention enhances mixing of the oxygen source and the active ionic liquid and, therefore, promotes the oxygen generation reaction.

Furthermore, the inventive devices can be construed in such a manner, that the orientation of the devices for generating oxygen in the gravity field of the earth is arbitrary. To this end, several oxygen outlets (sealed by gas permeable membranes or other structures allowing passage of oxygen, while blocking passage of non gaseous substances) must be provided in the walls of reaction chamber 2, and the openings must be arranged in such a manner that there is always an opening, which is not covered by ionic liquid, irrespective of the orientation of the device.

The invention claimed is:
1. A composition for generating oxygen, comprising
at least one oxygen source, and
at least one ionic liquid comprising a cation and an anion, wherein
said at least one oxygen source and said at least one ionic liquid are configured to generate oxygen gas upon coming into contact, and wherein
the oxygen source is a peroxide compound,
the ionic liquid is in the liquid state at least in a temperature range from −10° C. to +50° C., and
the anion is selected from metallate anions.

2. The composition according to claim 1, wherein the oxygen source and the ionic liquid are not in physical contact with each other.

3. The composition according to claim 1, wherein the oxygen source is selected from alkali metal percarbonates, alkali metal perborates, urea hydrogen peroxide, and mixtures thereof.

4. The composition according to claim 1, wherein the cation is selected from the group consisting of heterocyclic hydrocarbon cations, ammonium and phosphonium cations.

5. The composition according to claim 1, wherein the cation has at least one substituent, and wherein the cation may be symmetrically or asymmetrically disubstituted.

6. The composition according to claim 1, wherein the cation is selected from the group consisting of imidazolium, pyrrolidinium, ammonium, choline, pyridinium, pyrazolium, piperidinium, phosphonium, sulfonium cations.

7. The composition according to claim 1, wherein the metallate anion comprises at least one transition metal and at least one halide ion and/or pseudohalide ion.

8. The composition according to claim 7, wherein the transition metal is selected from iron and copper.

9. The composition according to claim 1, wherein the ionic liquid has the general formula $zC^+ \, MXy^{z-}$, wherein C represents a monovalent cation, M is selected from the group consisting of $Fe^{3+}$, $Fe^{2+}$ and $Cu^+$, and
when M is $Fe^{3+}$, y=4 and z=1,
when M is $Fe^{2+}$, y=4 and z=2, and
when M=$Cu^+$, y=2 and z=1.

10. The composition according to claim 9, wherein C represents a N,N'-disubstituted imidazolium cation, and wherein the substituents may be independently selected from the group consisting of methyl, hydroxy ethyl, butyl, hexyl, and octyl groups.

11. The composition according to claim 1, wherein the oxygen source is present in an amount ranging from 1 to 99 weight % of the composition and the ionic liquid is present in an amount ranging from 99 to 1 weight % of the composition.

12. The composition according to claim 1, wherein the oxygen source is in the form of a powder or in the form at least one powder compact, wherein the at least one powder compact has been compacted with a pressure in the range from 1 to 220 MPa.

13. The composition according to claim 1, wherein the composition is provided as a kit of at least two physically separated formulations, one of the formulations comprising the ionic liquid having a metallate anion, and the other formulation comprising the oxygen source.

14. The composition according to claim 1, wherein the oxygen source is an oxygen source formulation comprising two or more peroxide compounds and, optionally, at least one additive.

15. The composition according to claim 1, wherein the ionic liquid is an ionic liquid formulation comprising at least one active ionic liquid and, optionally, at least one non-active ionic liquid and, further optionally, at least one additive.

* * * * *